United States Patent
Certal et al.

(10) Patent No.: US 8,507,483 B2
(45) Date of Patent: Aug. 13, 2013

(54) 1H-PYRIMIDIN-2-ONE DERIVATIVES, PREPARATION THEREOF AND PHARMACEUTICAL USE THEREOF AS INHIBITORS OF AKT (PKB) PHOSPHORYLATION

(75) Inventors: Victor Certal, Paris (FR); Bruno Filoche-Rommé, Paris (FR); Frank Halley, Paris (FR); Karl Andreas Karlsson, Paris (FR); Fabienne Thompson, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/331,199

(22) Filed: Dec. 20, 2011

(65) Prior Publication Data

US 2012/0172360 A1 Jul. 5, 2012

Related U.S. Application Data

(63) Continuation of application No. PCT/FR2010/051376, filed on Jul. 1, 2010.

(60) Provisional application No. 61/241,101, filed on Sep. 10, 2009.

(30) Foreign Application Priority Data

Jul. 2, 2009 (FR) .................................... 09 03238
Oct. 9, 2009 (FR) .................................... 09 57073

(51) Int. Cl.
*A61K 31/535* (2006.01)
*C07D 413/14* (2006.01)

(52) U.S. Cl.
USPC .................. 514/233.8; 514/234.5; 544/123

(58) Field of Classification Search
USPC .................. 514/233.8, 234.5; 544/123
See application file for complete search history.

(56) References Cited

FOREIGN PATENT DOCUMENTS

WO  WO 03/024949 A1  3/2003
WO  WO 2006/109081 A1  10/2006

OTHER PUBLICATIONS

The International Search Report mailed on Sep. 13, 2010 for corresponding PCT/FR2010/051376 application.
The Written Opinion mailed on Sep. 13, 2010 for corresponding application PCT/FR2010/051376.

*Primary Examiner* — Rebecca Anderson
(74) *Attorney, Agent, or Firm* — Hamilton, Brook, Smith & Reynolds, P.C.

(57) ABSTRACT

The invention relates to the novel products of formula (I):

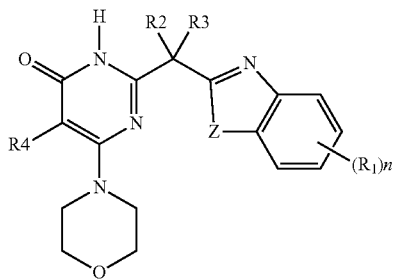

in which Z represents —O—, —NH or Nalk; n represents 0 to 4;
R1 represents Hal, hydroxyl, alkyl or alkoxy; the alkyl and alkoxy radicals being optionally substituted;
R2 and R3 represent H, Hal or alkyl optionally substituted with one or more halogen atoms;
R4 represents H;
these products being in all the isomer forms and the salts, as medicaments, in particular as inhibitors of AKT(PKB) phosphorylation.

14 Claims, No Drawings

1H-PYRIMIDIN-2-ONE DERIVATIVES, PREPARATION THEREOF AND PHARMACEUTICAL USE THEREOF AS INHIBITORS OF AKT (PKB) PHOSPHORYLATION

APPLICATIONS

This application is a continuation of International Application No. PCT/FR2010/051376, which designated the United States and was filed on Jul. 1, 2010 which claims the benefit of priority of French Patent Application No. 0903238, filed Jul. 2, 2009, and claims the benefit of U.S. Provisional Application No. 61/241,101, filed on Sep. 10, 2009, and French Patent Application No. 0957073, filed Oct. 9, 2009 all of which are incorporated herein by reference.

The entire teachings of the above applications are incorporated herein by reference.

SUMMARY OF THE INVENTION

The present invention relates to novel 1H-pyrimidin-2-one chemical compounds derived from pyrimidinones, to the process for the preparation thereof, to the novel intermediates obtained, to the use thereof as medicaments, to the pharmaceutical conditions containing them and to the novel use of such derivatives.

The present invention thus also relates to the use of said derivatives for the preparation of a medicament for use in treating humans.

More particularly, the invention relates to novel pyrimidinone derivatives and to the pharmaceutical use thereof for the prevention and treatment of conditions capable of being modulated by inhibition of the PI3K/AKT/mTOR pathway. AKT is a key participant in this signalling pathway. A high level of AKT phosphorylation is the mark of the activation of the pathway, which is found in many human cancers.

The products of the present invention may thus in particular be used for the prevention or treatment of conditions capable of being modulated by inhibition of AKT phosphorylation (P-AKT). The inhibition of P-AKT may especially be obtained by inhibition of the PI3K/AKT/mTOR pathway, and in particular by inhibition of kinases belonging to this pathway, for instance receptor tyrosine kinases such as EGFR, IGFR, ErbB2,3'-phosphoinositide-dependent protein kinase-1 (PDK1), the PI3K phosphoinositide kinase, the AKT serine-threonine kinase, or the mTOR kinase.

The inhibition and regulation of the PI3K/AKT/mTOR pathway constitutes in particular a new and powerful mechanism of action for the treatment of a large number of cancer diseases including solid and liquid tumours.

Such conditions that can be treated by the products of the present application are solid or liquid human tumours.

Role of the PI3K/AKT/mTOR pathway

The PI3K/AKT/mTOR signalling pathway is a complex network which regulates multiple cell functions, such as growth, survival, proliferation and cell growth, which are key processes in tumorigenesis.

This signalling pathway is an important target in the treatment of cancer since most of its effectors are altered in human tumours. The principle effectors contributing to the activation of the pathway are i) oncogenes, such as ErbB1 (EGFR), ErbB2 (HER2), PIK3CA and AKT, activated by mutation, amplification or overexpression; ii) the deficiency in tumour suppressor genes such as PTEN, TSC1/2, LKB and PML, which are inactivated following mutations or deletions (Jiang L-Z & Liu L-Z, Biochim Biophys Acta, 2008, 1784:150; Vivanco I & Sawyers C L, 2002, Nat Rev Cancer, 2:489; Cully M et al., Nature Rev. Cancer, 2006, 6:184).

The activation of the oncogenes of this signalling pathway is found in many human cancer diseases:
PIK3CA activating mutations are present in 15-30% of colon, breast, endometrial, liver, ovarian and prostate cancers (T L Yuan and L C Cantley, Oncogene, 2008, 27:5497; Y. Samuels et al. Science, 2004, 304:554; KE. Bachman et al. Cancer Biol Ther, 2004, 3:772; DA Levine et al. Clin Canc Res. 2005, 11:2875; C. Hartmann et al. Acta Neuropathol. 2005, 109:639);
amplifications, activating mutations and overexpressions of RTKs such as EGFR and HER2 in brain, breast and lung (NSCLC) cancers;
amplification and activating overexpression of AKT in brain, lung (NSCLC), breast, kidney, ovarian and pancreatic cancers (Testa J R. and Bellacosa A., Proct. Natl. Acad. Sci. USA 2001, 98:10983; Cheng et al., Proct. Natl. Acad. Sci. USA 1992, 89: 9267; Bellacosa et al., Int. J. Cancer, 1995, 64:280; Cheng et al., Proct. Natl. Acad. Sci. USA 1996, 93:3636; Yuan et al., Oncogene, 2000, 19:2324).

Deficiency in the tumour suppressor genes of this signalling pathway is also found in many human cancer diseases:
deletion of PTEN in 50% of lung (NSCLC), liver, kidney, prostate, breast, brain, pancreatic, endometrial and colon cancers (Maxwell G L et al. Canc. Res. 1998, 58:2500; Zhou X-P et al. Amer. J. Pathol., 2002, 161: 439; Endersby R & Baker S J, Oncogene, 2008, 27:5416; Li et al. Science, 1997, 275:1943; Steack P A et al., Nat. Genet., 1997, 15:356);
mutations in TSC1/2 in more than 50% of tuberous scleroses;
mutations or deletions in LKB1 (or STK11) which predispose to gastrointestinal tract cancers and to pancreatic cancer and which are found in particular in 10-38% of lung adenocarcinomas (Shah U. et al. Cancer Res. 2008, 68:3562);
modifications of PML in particular by translocation in human tumours (Gurrieri C et al, J. NAtl Cancer Inst. 2004, 96:269).

In addition, this signalling pathway is a major factor for resistance to chemotherapy, to radiotherapy and to targeted therapies such as EGFR and HER2, for example (C. Sawyers et al. Nat Rev 2002).

Role of AKT

AKT (protein kinase B; PKB) is a serine-threonine kinase which occupies a central place in one of the major cell signalling pathways, the PI3K/AKT pathway. AKT is in particular involved in the growth, proliferation and survival of tumour cells. AKT activation occurs in two steps, (i) by phosphorylation of threonine 308 (P-T308) by PDK1 and (2) by phosphorylation of serine 473-(P-5473) by mTORC2 (or mTOR-Rictor complex), resulting in complete activation. AKT in turn regulates a large number of proteins, including mTOR (mammalian target of Rapamycin), BAD, GSK3, p21, p27, FOXO or FKHRL1 (Manning B D & Cantley L C, Cell, 2007 129:1261). The activation of AKT promotes the internalisation of nutrients, thereby triggering a process of anabolising metabolization supporting cell growth and proliferation. In particular, AKT controls the initiation of protein synthesis through a cascade of interactions that occurs by means of TSC1/2 (tuberous scleroses complex), Rheb and TOR, so as to result in two essential targets of the signalling pathway, p70S6K and 4EBP. AKT also induces inhibiting phosphorylation of the Forkhead transcription factor and inactivation of GSK3β, which result in the inhibition of apoptosis and in progression of the cell cycle (Franke T F, Oncogene, 2008, 27:6473). AKT is therefore a target for anticancer therapy and the inhibition of AKT activation by inhibition of the phosphorylation thereof may induce apoptosis of malignant cells and, by the same token, provide a treatment for cancer.

Receptor Tyrosine Kinases Such as IGF1R

Abnormally high levels of protein kinase activity have been implicated in many diseases resulting from abnormal cell functions. This may originate either directly or indirectly from a dysfunction in the mechanisms for controlling the kinase activity, related to for example an inappropriate mutation, overexpression or activation of the enzyme, or owing to an overproduction or underproduction of cytokines or of growth factors, also involved in the transduction of upstream or downstream signals of kinases. In all these cases, a selective inhibition of the action of kinases leads to the hope of a beneficial effect.

The insulin-like growth factor type 1 receptor (IGF-I-R) is a transmembrane receptor tyrosine kinase which binds firstly to IGFI, but also to IGFII and to insulin with a weak affinity. The binding of IGF1 to its receptor leads to oligomerization of the receptor, activation of the tyrosine kinase, intermolecular autophosphorylation and phosphorylation of cell substrates (principal substrates: IRS1 and Shc). The receptor activated by its ligand induces a mitogenic activity in normal cells. However, IGF-I-R plays an important role in "abnormal" growth.

Several clinical reports underline the important role of the IGF-I pathway in the development of human cancers:

IGF-I-R is often found overexpressed in many tumour types (breast, colon, lung, sarcoma, prostate, multiple myeloma) and its presence is often associated with a more aggressive phenotype.

High concentrations of circulating IGF1 are strongly correlated with a risk of prostate, lung and breast cancer.

Furthermore, it has been widely documented that IGF-I-R is necessary for the establishment and maintenance of the transformed phenotype in vitro just as in vivo [Baserga R, Exp. Cell. Res., 1999, 253, pages 1-6]. The kinase activity of IGF-I-R is essential for the transforming activity of several oncogenes: EGFR, PDGFR, SV40 virus broad T antigen, activated Ras, Raf, and v-Src. The expression of IGF-I-R in normal fibroblasts induces a neoplastic phenotype, which can subsequently lead to tumour formation in vivo. IGF-I-R expression plays an important role in substrate-independent growth. IGF-I-R has also been shown to be a protector in chemotherapy- and radiation-induced apoptosis and cytokine-induced apoptosis. Furthermore, the inhibition of endogenous IGF-I-R by a dominant negative, the formation of a triple helix or the expression of an antisense causes a suppression of the transforming activity in vitro and a decrease in tumour growth in animal models.

PDK1

3'-Phosphoinositide-dependent protein kinase-1 (PDK1) is one of the essential components of the PI3K-AKT signalling pathway. It is a serine-threonine (Ser/Thr) kinase, the role of which is to phosphorylate and activate other Ser/Thr kinases of the AGC family that are involved in the control of cell growth, proliferation and survival and in the regulation of the metabolism. These kinases include protein kinase B (PKB or AKT), SGK (or serum and glucocorticoid regulated kinase), RSK (or p90 ribosomal S6 kinase), p70S6K (or p70 ribosomal S6 kinase) and also various isoforms of protein kinase C(PKC) (Vanhaesebroeck B. & Alessi D R., Biochem J, 2000, 346:561). One of the key roles of PDK1 is therefore the activation of AKT: in the presence of PIP3, which is the second messenger generated by PI3K, PDK-1 is recruited to the plasma membrane via its PH (pleckstrin homology) domain and phosphorylates AKT on threonine 308 located in the activation loop, which is an essential modification for AKT activation. PDK1 is expressed ubiquitously and is a constitutively activate kinase. PDK1 is a key element in the PI3K/AKT signalling pathway for regulating key processes in tumorigenesis, such as cell proliferation and survival. Since this pathway is activated in more than 50% of human cancers, PDK1 represents a target for anticancer therapy. The inhibition of PDK1 should result in an effective inhibition of the proliferation and survival of cancer cells and therefore provide a therapeutic benefit for human cancers (Bayascas J R, Cell cycle, 2008, 7:2978; Peifer C. & Alessi D R, Chem Med Chem, 2008, 3:1810).

Phosphoinositide 3-kinases (PI3Ks)

The PI3K lipid kinase is an important target in this signalling pathway for oncology. The class I PI3Ks are divided up into class Ia (PI3K$\alpha,\beta,\delta$) activated by receptor tyrosine kinases (RTKs), G protein-coupled receptors (GPCRs), GTPases of the family Rho, p21-Ras, and class Ib (PI3K$\gamma$) activated by GPCRs and p21-Ras. The class Ia PI3Ks are heterodimers which consist of a catalytic subunit p110$\alpha$, $\beta$ or $\delta$ and a regulatory subunit p85 or p55. The class Ib (p110$\gamma$) is monomeric. The class I PI3Ks are lipid/protein kinases which are activated by RTKs, GPCRs or Ras after recruitment of the membrane. These class I PI3Ks phosphorylate phosphatidylinositol 4,5-diphosphate (PIP2) on position 3 of the inositol so as to give phosphatidylinositol 3,4,5-triphosphate (PIP3), a key secondary messenger in this signalling pathway. In turn, PIP3 recruits AKT and PDK1 to the membrane, where they bind via their pleckstrin homology domain (PH domain), resulting in activation of AKT by PDK1 phosphorylation on threonine 308. AKT phosphorylates many substrates, thus playing a key role in many processes resulting in cell transformation, such as cell proliferation, growth and survival, and also angiogenesis.

The class I PI3Ks are implicated in human cancers: somatic mutations of the PIK3CA gene, which encodes PI3K$\alpha$, are found in 15-35% of human tumours, with in particular two principle oncogenic mutations, H1047R (in the kinase domain), and E545K/E542K (in the helical domain), (Y. Samuels et al. Science, 2004, 304:554; T L Yuan and L C Cantley, Oncogene, 2008, 27:5497). PI3K inhibitors are expected to be effective in the treatment of many human cancers exhibiting genetic alterations resulting in the activation of the PI3K/AKT/mTOR pathway (Vogt P. et al., Virology, 2006, 344:131; Zhao L & Vogt P K, Oncogene, 2008, 27:5486).

Kinase-inhibiting morpholinopyrimidinone derivatives are known to those skilled in the art.

Application WO 2008/148074 describes products which have an mTOR-inhibiting activity. These products are pyrido[1,2-a]pyrimidin-4-ones which differ from the products of the present invention owing to their entirely aromatic nature and their substitutions.

Application WO 2008/064244 describes the application of the PI3K$\beta$-inhibiting products TGX-221 and TGX-155 that are of use in the treatment of cancer, and in particular of breast cancer. These products are pyrido[1,2-a]pyrimidin-4-ones previously described in applications WO 2004/016607 and WO 2001/053266, which differ from the products of the present invention owing to their entirely aromatic nature and their substitutions.

Applications WO 2006/109081, WO 2006/109084 and WO 2006/126010 describe DNA-PK-inhibiting products that are of use in the treatment of ATM-deficient cancers. These products are pyrido[1,2-a]pyrimidin-4-ones which differ from the products of the present invention owing to their entirely aromatic nature and their substitutions.

Application WO 2003/024949 describes DNA-PK-inhibiting products that are of use in the treatment of ATM-deficient cancers. These products are pyrido[1,2-a]pyrimidin-4-ones which differ from the products of the present invention owing to their entirely aromatic nature and their substitutions.

Kinase-inhibiting morpholinopyrimidine derivatives are also known from the prior art.

Applications WO 2009/007748, WO 2009/007749, WO 2009/007750 and WO 2009/007751 describe products which have an mTOR- and/or PI3K-inhibiting activity in the treatment of cancers. These products are pyrimidines substituted in the 2-, 4- and 6-positions, and the products of the present invention differ therefrom owing to the presence of the carbonyl group on the pyrimidinone, and also by virtue of the various substituents.

A subject of the present invention is the products of the formula (I):

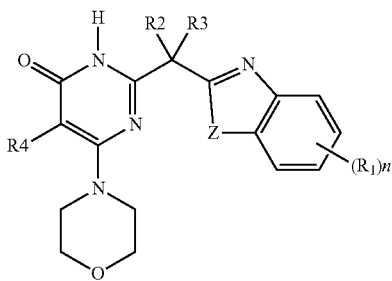

in which:
Z represents —O—, —NH, N-cycloalkyl, Nalk or N-phenyl, with alk and phenyl optionally substituted with one or more radicals chosen from halogen atoms, and alkyl, alkoxy, hydroxyl, cyano and phenyl radicals, said phenyl radical being itself optionally substituted with one or more radicals chosen from halogen atoms and hydroxyl, alkoxy and alkyl radicals;
n represents an integer from 0 to 4;
R1 represents a hydrogen atom, a halogen atom or a hydroxyl, alkyl or alkoxy radical;
the alkyl and alkoxy radicals being optionally substituted with an NRxRy group or with one or more halogen atoms;
it being understood that R1 can represent a phenyl residue fused with the phenyl which bears R1 so as to form a naphthyl;
R2 and R3, which may be identical or different, represent a hydrogen atom, a halogen atom, or an alkyl radical optionally substituted with one or more halogen atoms;
R4 represents a hydrogen atom;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted with one or more radicals, which may be identical or different, chosen from halogen atoms and alkyl, hydroxyl, oxo, alkoxy, NH$_2$, NHalk and N(alk)$_2$ radicals;
all of the above alkyl (alk) and alkoxy radicals being linear or branched and containing from 1 to 6 carbon atoms, said products of formula (I) being in all the possible racemic, enantiomeric and diastereoisomeric isomer forms, and also the addition salts with inorganic and organic acids or with inorganic and organic bases, of said products of formula (I).

A subject of the present invention is thus the products of formula (I) as defined above, in which:
Z represents —O—, —NH, N-cycloalkyl, Nalk or N-phenyl, with alk optionally substituted with one or more radicals chosen from alkoxy, hydroxyl, cyano and phenyl;
n represents an integer from 0 to 4;
R1 represents a hydrogen atom, a halogen atom or an alkyl or alkoxy radical; the alkyl and alkoxy radicals being optionally substituted with an NRxRy group or with one or more halogen atoms; it being understood that R1 can represent a phenyl residue fused with the phenyl which bears R1 so as to form a naphthyl radical;
R2 and R3 represent a hydrogen atom;
R4 represents a hydrogen atom;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;
all the above alkyl (alk) and alkoxy radicals being linear or branched and containing from 1 to 6 carbon atoms,
said products of formula (I) being in all the possible racemic, enantiomeric and diastereoisomeric isomer forms, and also the addition salts with inorganic and organic acids or with inorganic and organic bases, of said products of formula (I).

A subject of the present invention is the products of formula (I):

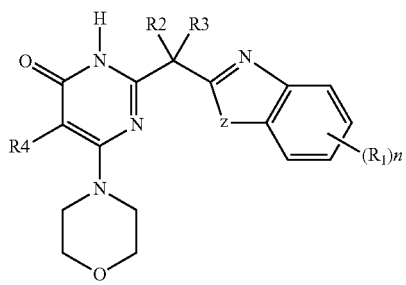

in which:
Z represents —O—, —NH, Nalk or N-phenyl optionally substituted with one or more radicals chosen from halogen atoms, and the alkyl, alkoxy and hydroxyl radicals;
n represents an integer from 0 to 4;
R1 represents a hydrogen atom, a halogen atom or a hydroxyl, alkyl or alkoxy radical;
the alkyl and alkoxy radicals being optionally substituted with an NRxRy group;
R2 and R3, which may be identical or different, represent a hydrogen atom, a halogen atom, or an alkyl radical optionally substituted with one or more halogen atoms;
R4 represents a hydrogen atom;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted with one or more radicals which may be identical or different, chosen from halogen atoms and alkyl, hydroxyl, oxo, alkoxy, NH$_2$, NHalk and N(alk)$_2$ radicals;
all the above alkyl (alk) and alkoxy radicals being linear or branched and containing from 1 to 6 carbon atoms,
said products of formula (I) being in all the possible racemic, enantiomeric and diastereoisomeric isomer forms, and also the addition salts with inorganic and organic acids or with inorganic and organic bases, of said products of formula (I).
A subject of the present invention is the products of formula (I) as defined above:

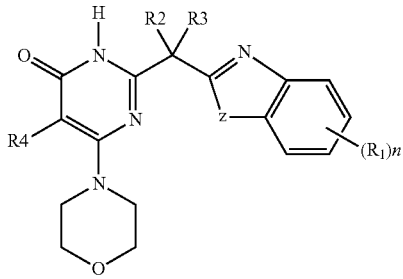

in which:
Z represents —O—, —NH or Nalk;
n represents an integer from 0 to 4;
R1 represents a halogen atom or a hydroxyl, alkyl or alkoxy radical; the alkyl and alkoxy radicals being optionally substituted with an NRxRy group;
R2 and R3, which may be identical or different, represent a hydrogen atom, a halogen atom, or an alkyl radical optionally substituted with one or more halogen atoms;
R4 represents a hydrogen atom;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted with one or more radicals, which may be identical or different, chosen from halogen atoms and alkyl, hydroxyl, oxo, alkoxy, NH$_2$, NHalk and N(alk)$_2$ radicals;
said products of formula (I) being in all the possible racemic, enantiomeric and diastereoisomeric isomer forms, and also the addition salts with inorganic and organic acids or with inorganic and organic bases, of said products of formula (I).
  In the products of formula (I):
  the term "alkyl (or alk) radical" denotes the linear, and where appropriate branched, radicals methyl, ethyl, propyl, isopropyl, butyl, isobutyl, sec-butyl, tert-butyl, pentyl, isopentyl, hexyl, isohexyl and also heptyl, octyl, nonyl and decyl, and also the linear or branched positional isomers thereof: the alkyl radicals containing from 1 to 6 carbon atoms and more particularly the alkyl radicals containing from 1 to 4 carbon atoms of the above list are preferred;
  the term "alkoxy radical" denotes the linear, and where appropriate branched, radicals methoxy, ethoxy, propoxy, isopropoxy, linear, secondary or tertiary butoxy, pentoxy or hexoxy, and also the linear or branched positional isomers thereof: the alkoxy radicals containing from 1 to 4 carbon atoms of the above list are preferred;
  the term "alkylthio radical" denotes the linear, and where appropriate branched, radicals methylthio, ethylthio, propylthio, isopropylthio, linear, secondary or tertiary butylthio, pentylthio or hexylthio, and also the linear or branched positional isomers thereof: the alkylthio radicals containing from 1 to 4 carbon atoms of the above list are preferred;
  the term "halogen atom" denotes chlorine, bromine, iodine or fluorine atoms, and preferably the chlorine, bromine or fluorine atom;
  the term "cycloalkyl radical" denotes a saturated carbocyclic radical containing 3 to 10 carbon atoms and thus denotes in particular cyclopropyl, cyclobutyl, cyclopentyl and cyclohexyl radicals, and most particularly cyclopropyl, cyclopentyl and cyclohexyl radicals;
  in the —O-cycloalkyl radical, cycloalkyl is as defined above;
  the term "heterocycloalkyl radical" thus denotes a monocyclic or bicyclic carbocyclic radical containing from 3 to 10 ring members, interrupted with one or more heteroatoms, which may be identical or different, chosen from oxygen, nitrogen or sulphur atoms: mention may, for example, be made of morpholinyl, thiomorpholinyl, homomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, tetrahydropyran, oxodihydropyridazinyl or else oxetanyl radicals, all these radicals being optionally substituted; mention may in particular be made of morpholinyl, thiomorpholinyl, homomorpholinyl, piperazinyl, piperidyl, homopiperazinyl or else pyrrolidinyl radicals;
  the terms "aryl" and "heteroaryl" denote monocyclic or bicyclic, respectively carbocyclic and heterocyclic, unsaturated or partially unsaturated radicals containing at most 12 ring members, that may optionally contain a —C(O) ring member, the heterocyclic radicals containing one or more heteroatoms, which may be identical or different, chosen from O, N, or S, with N, where appropriate, being optionally substituted;
  the term "aryl radical" thus denotes monocyclic or bicyclic radicals containing 6 to 12 ring members, such as, for example, phenyl, naphthyl, biphenyl, indenyl, fluorenyl and anthracenyl radicals, more particularly phenyl and naphthyl radicals, and even more particularly the phenyl radical. It may be noted that a carbocyclic radical containing a —C(O) ring member is, for example, the tetralone radical;
  the term "heteroaryl radical" thus denotes monocyclic or bicyclic radicals containing 5 to 12 ring members: monocyclic heteroaryl radicals such as, for example, the radicals: thienyl, such as 2-thienyl and 3-thienyl, furyl, such as 2-furyl or 3-furyl, pyranyl, pyrrolyl, pyrrolinyl, pyrazolinyl, imidazolyl, pyrazolyl, pyridyl, such as 2-pyridyl, 3-pyridyl and 4-pyridyl, pyrazinyl, pyrimidinyl, pyridazinyl, oxazolyl, thiazolyl, isothiazolyl, diazolyl, thiadiazolyl, thiatriazolyl, oxadiazolyl, isoxazolyl, such as 3- or 4-isoxazolyl, furazanyl, free or salified tetrazolyl, all these radicals being optionally substituted, among which are more particularly the radicals: thienyl, such as 2-thienyl and 3-thienyl, furyl, such as 2-furyl, pyrrolyl, pyrrolinyl, pyrazolinyl, imidazolyl, pyrazolyl, oxazolyl, isoxazolyl, pyridyl and pyridazinyl, these radicals being optionally substituted; bicyclic heteroaryl radicals such as, for example, the radicals: benzothienyl, such as 3-benzothienyl, benzothiazolyl, quinolyl, isoquinolyl, dihydroquinolyl, quinolone, tetralone, adamentyl, benzofuryl, isobenzofuryl, dihydrobenzofuran, ethylenedioxyphenyl, thianthrenyl, benzopyrrolyl, benzimidazolyl, benzoxazolyl, thionaphthyl, indolyl, azaindolyl, indazolyl, purinyl, thienopyrazolyl, tetrahydroindazolyl, tetrahydrocyclopentapyrazolyl, dihydrofuropyrazolyl, tetrahydropyrrolopyrazolyl, oxotetrahydropyrrolopyrazolyl, tetrahydropyranopyrazolyl, tetrahydropyridinopyrazolyl or oxodihydropyridinopyrazolyl, all these radicals being optionally substituted.

As examples of heteroaryl or bicyclic radicals, mention may more particularly be made of pyrimidinyl, pyridyl, pyrrolyl, azaindolyl, indazolyl or pyrazolyl, benzothiazolyl or benzimidazolyl radicals optionally substituted with one or more substituents, which may be identical or different, as indicated above.

The carboxyl radical(s) of the products of formula (I) may be salified or esterified with the various groups known to those skilled in the art, among which mention may be made, for example of:

among the salification compounds, inorganic bases such as, for example, an equivalent of sodium, of potassium, of lithium, of calcium, of magnesium or of ammonium, or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine and N-methylglucamine;

among the esterification compounds, the alkyl radicals for forming alkoxycarbonyl groups, such as, for example, methoxycarbonyl, ethoxycarbonyl, tert-butoxycarbonyl or benzyloxycarbonyl, it being possible for these alkyl radicals to be substituted with radicals chosen, for example, from halogen atoms and hydroxyl, alkoxy, acyl, acyloxy, alkylthio, amino or aryl radicals, as, for example, in chloromethyl, hydroxypropyl, methoxymethyl, propionyloxymethyl, methylthiomethyl, dimethylaminoethyl, benzyl or phenethyl groups.

The addition salts with inorganic or organic acids of the products of formula (I) may, for example, be the salts formed with hydrochloric acid, hydrobromic acid, hydroiodic acid, nitric acid, sulphuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkoylmonosulphonic acids such as, for example, methanesulphonic acid, ethanesulphonic acid or propanesulphonic acid, alkoyldisulphonic acids such as, for example, methanedisulphonic acid or alpha, beta-ethanedisulphonic acid, arylmonosulphonic acids such as benzenesulphonic acid, and aryldisulphonic acids.

It may be recalled that stereoisomerism can be defined in its broad sense as the isomerism of compounds having the same structural formulae, but the various groups of which are arranged differently in space, such as in particular in monosubstituted cyclohexanes in which the substituent may be in the axial or equatorial position, and the various possible rotational conformations of ethane derivatives. However, another type of stereoisomerism exists, due to the different spatial arrangements of fixed substituents, on double bonds or on rings, which is often referred to as geometrical isomerism or cis-transisomerism. The term "stereoisomers" is used in the present application in its broadest sense and therefore relates to all the compounds indicated above.

A subject of the present invention is the products of formula (I) as defined above, in which:
Z represents —O—, —NH, Nalk or N-phenyl;
n represents an integer from 0 to 4;
R2 and R3 represent a hydrogen atom;
R4 represents a hydrogen atom;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;
all the above alkyl (alk) and alkoxy radicals being linear or branched and containing from 1 to 6 carbon atoms,
said products of formula (I) being in all the possible racemic, enantiomeric and diastereoisomeric isomer forms, and also the addition salts with inorganic and organic acids or with inorganic and organic bases, of said products of formula (I).

A subject of the present invention is the products of formula (I) as defined above, in which:
Z represents —O—, —NH or Nalk;
n represents an integer from 0 to 4;
R1 represents a halogen atom or an alkyl or alkoxy radical;
R2 and R3 represent a hydrogen atom;
R4 represents a hydrogen atom;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;
all the above alkyl (alk) and alkoxy radicals being linear or branched and containing from 1 to 6 carbon atoms,
said products of formula (I) being in all the possible racemic, enantiomeric and diastereoisomeric isomer forms, and also the addition salts with inorganic and organic acids or with inorganic and organic bases, of said products of formula (I).

In particular, when NRxRy forms a ring as defined above, such an amine ring may be chosen in particular from pyrrolidinyl, pyrazolidinyl, pyrazolinyl, piperidyl, azepinyl, morpholinyl, homomorpholinyl, piperazinyl or homopiperazinyl radicals, these radicals being themselves optionally substituted as indicated above or hereinafter. The NRxRy ring may more particularly be chosen from the radicals: pyrrolidinyl, morpholinyl optionally substituted with one or two alkyl radicals or piperazinyl optionally substituted on the second nitrogen atom with an alkyl, phenyl, or and CH₂-phenyl radical, themselves optionally substituted with one or more radicals, which may be identical or different, chosen from halogen atoms and alkyl, hydroxyl and alkoxy radicals.

A subject of the present invention is thus most particularly the products of formula (I) as defined above, corresponding to the following formulae:
2-[(5-fluoro-1H-benzimidazol-2-yl)methyl]-6-(morpholin-4-yl)pyrimidin-4(3H)-one
2-(1,3-benzoxazol-2-ylmethyl)-6-(morpholin-4-yl)pyrimidin-4(3H)-one
2-[(6-bromo-1H-benzimidazol-2-yl)methyl]-6-(morpholin-4-yl)pyrimidin-4(3H)-one
2-[(6-methoxy-1H-benzimidazol-2-yl)methyl]-6-(morpholin-4-yl)pyrimidin-4(3H)-one
2-[(5,6-difluoro-1H-benzimidazol-2-yl)methyl]-6-(morpholin-4-yl)pyrimidin-4(3H)-one 2-[(6-fluoro-1,3-benzoxazol-2-yl)methyl]-6-(morpholin-4-yl)pyrimidin-4(3H)-one
2-[(5-fluoro-1,3-benzoxazol-2-yl)methyl]-6-(morpholin-4-yl)pyrimidin-4(3H)-one
2-[(6-methyl-1,3-benzoxazol-2-yl)methyl]-6-(morpholin-4-yl)pyrimidin-4(3H)-one
2-[(6-bromo-1,3-benzoxazol-2-yl)methyl]-6-(morpholin-4-yl)pyrimidin-4(3H)-one
2-[(1-methyl-1H-benzimidazol-2-yl)methyl]-6-(morpholin-4-yl)pyrimidin-4(3H)-one
2-[(5-fluoro-1-methyl-1H-benzimidazol-2-yl)methyl]-6-(morpholin-4-yl)pyrimidin-4(3H)-one
2-[(7-fluoro-1,3-benzoxazol-2-yl)methyl]-6-(morpholin-4-yl)pyrimidin-4(3H)-one
6-(morpholin-4-yl)-2-[(1-phenyl-1H-benzimidazol-2-yl)methyl]pyrimidin-4(3H)-one
2-[(1-benzyl-1H-benzimidazol-2-yl)methyl]-6-(morpholin-4-yl)pyrimidin-4(3H)-one
2-[(1-ethyl-1H-benzimidazol-2-yl)methyl]-6-(morpholin-4-yl)pyrimidin-4(3H)-one
2-[(5,6-difluoro-1,3-benzoxazol-2-yl)methyl]-6-(morpholin-4-yl)pyrimidin-4(3H)-one
2-[(6-chloro-1H-benzimidazol-2-yl)methyl]-6-(morpholin-4-yl)pyrimidin-4(3H)-one
2-[(1-cyclopropyl-5-fluoro-1H-benzimidazol-2-yl)methyl]-6-(morpholin-4-yl)pyrimidin-4(3H)-one
2-{[5-fluoro-1-(2-methoxyethyl)-1H-benzimidazol-2-yl]methyl}-6-(morpholin-4-yl)pyrimidin-4(3H)-one
6-(morpholin-4-yl)-2-(naphtho[2,1-d][1,3]oxazol-2-ylmethyl)pyrimidin-4(3H)-one
2-[(6-methoxy-1,3-benzoxazol-2-yl)methyl]-6-(morpholin-4-yl)pyrimidin-4(3H)-one
2-[(6,7-difluoro-1,3-benzoxazol-2-yl)methyl]-6-(morpholin-4-yl)pyrimidin-4(3H)-one
2-[(5,6-dichloro-1H-benzimidazol-2-yl)methyl]-6-(morpholin-4-yl)pyrimidin-4(3H)-one
2-[(6-methyl-1H-benzimidazol-2-yl)methyl]-6-(morpholin-4-yl)pyrimidin-4(3H)-one
2-{[4-chloro-6-(trifluoromethyl)-1H-benzimidazol-2-yl]methyl}-6-(morpholin-4-yl)pyrimidin-4(3H)-one
6-(morpholin-4-yl)-2-{[6-(trifluoromethyl)-1H-benzimidazol-2-yl]methyl}pyrimidin-4(3H)-one
2-[(5-chloro-6-fluoro-1H-benzimidazol-2-yl)methyl]-6-(morpholin-4-yl)pyrimidin-4(3H)-one
2-[(6,7-difluoro-1H-benzimidazol-2-yl)methyl]-6-(morpholin-4-yl)pyrimidin-4(3H)-one
2-[(5-chloro-6-methyl-1H-benzimidazol-2-yl)methyl]-6-(morpholin-4-yl)pyrimidin-4(3H)-one
(2-{[4-(morpholin-4-yl)-6-oxo-1,6-dihydropyrimidin-2-yl]methyl}-1H-benzimidazol-1-yl)acetonitrile
2-[(5,7-difluoro-1H-benzimidazol-2-yl)methyl]-6-(morpholin-4-yl)pyrimidin-4(3H)-one
2-{[5-chloro-1-(1-phenylethyl)-1H-benzimidazol-2-yl]methyl}-6-(morpholin-4-yl)pyrimidin-4(3H)-one
2-[(1-cyclohexyl-1H-benzimidazol-2-yl)methyl]-6-(morpholin-4-yl)pyrimidin-4(3H)-one
6-(morpholin-4-yl)-2-[(5,6,7-trifluoro-1H-benzimidazol-2-yl)methyl]pyrimidin-4(3H)-one
2-[(4-bromo-6-fluoro-1H-benzimidazol-2-yl)methyl]-6-(morpholin-4-yl)pyrimidin-4(3H)-one
2-[(6-bromo-1-methyl-1H-benzimidazol-2-yl)methyl]-6-(morpholin-4-yl)pyrimidin-4(3H)-one
2-[(6,7-difluoro-1-methyl-1H-benzimidazol-2-yl)methyl]-6-(morpholin-4-yl)pyrimidin-4(3H)-one
2-[(5,6-dichloro-1-methyl-1H-benzimidazol-2-yl)methyl]-6-(morpholin-4-yl)pyrimidin-4(3H)-one
6-(morpholin-4-yl)-2-[(5,6,7-trifluoro-1-methyl-1H-benzimidazol-2-yl)methyl]pyrimidin-4(3H)-one
2-[(4-hydroxy-1,3-benzoxazol-2-yl)methyl]-6-(morpholin-4-yl)pyrimidin-4(3H)-one
2-[(7-bromo-1-methyl-1H-benzimidazol-2-yl)methyl]-6-(morpholin-4-yl)pyrimidin-4(3H)-one
and also the addition salts with inorganic and organic acids or with inorganic and organic bases, of said products of formula (I).

A subject of the present invention is most particularly the products of formula (I) as defined above, corresponding to the following formulae:
2-[(5-fluoro-1H-benzimidazol-2-yl)methyl]-6-(morpholin-4-yl)pyrimidin-4(3H)-one
2-(1,3-benzoxazol-2-ylmethyl)-6-(morpholin-4-yl)pyrimidin-4(3H)-one
2-[(6-bromo-1H-benzimidazol-2-yl)methyl]-6-(morpholin-4-yl)pyrimidin-4(3H)-one
2-[(6-methoxy-1H-benzimidazol-2-yl)methyl]-6-(morpholin-4-yl)pyrimidin-4(3H)-one
2-[(5,6-difluoro-1H-benzimidazol-2-yl)methyl]-6-(morpholin-4-yl)pyrimidin-4(3H)-one
2-[(6-fluoro-1,3-benzoxazol-2-yl)methyl]-6-(morpholin-4-yl)pyrimidin-4(3H)-one
2-[(5-fluoro-1,3-benzoxazol-2-yl)methyl]-6-(morpholin-4-yl)pyrimidin-4(3H)-one
2-[(6-methyl-1,3-benzoxazol-2-yl)methyl]-6-(morpholin-4-yl)pyrimidin-4(3H)-one
2-[(6-bromo-1,3-benzoxazol-2-yl)methyl]-6-(morpholin-4-yl)pyrimidin-4(3H)-one
2-[(1-methyl-1H-benzimidazol-2-yl)methyl]-6-(morpholin-4-yl)pyrimidin-4(3H)-one
2-[(5-fluoro-1-methyl-1H-benzimidazol-2-yl)methyl]-6-(morpholin-4-yl)pyrimidin-4(3H)-one
2-[(7-fluoro-1,3-benzoxazol-2-yl)methyl]-6-(morpholin-4-yl)pyrimidin-4(3H)-one
6-(morpholin-4-yl)-2-[(1-phenyl-1H-benzimidazol-2-yl)methyl]pyrimidin-4(3H)-one
and also the addition salts with inorganic and organic acids or with inorganic and organic bases, of said products of formula (I).

A subject of the present invention is in particular products of formula (I) as defined above, corresponding to the following formula:
2-[(1-methyl-1H-benzimidazol-2-yl)methyl]-6-(morpholin-4-yl)pyrimidin-4(3H)-one
and also the addition salts with inorganic and organic acids or with inorganic and organic bases, of said products of formula (I).

A subject of the present invention is also any process for preparing the products of formula (I) as defined above.

The products according to the invention can be prepared using conventional organic chemistry methods.

Preparation of Compounds of Formula (I)

The products of general formula (I) according to the present invention can in particular be prepared as indicated in general schemes 1A-1B below. In this respect, the methods described cannot constitute a limitation of the scope of the invention, as regards the methods for preparing the claimed compounds.

The preparations of the examples of the present invention give illustrations of the schemes below.

Such synthesis schemes are part of the present invention: a subject of the present invention is thus also the processes for preparing the products of formula C to (I)-b, as defined in general schemes 1A-1B below.

General Scheme 1A:

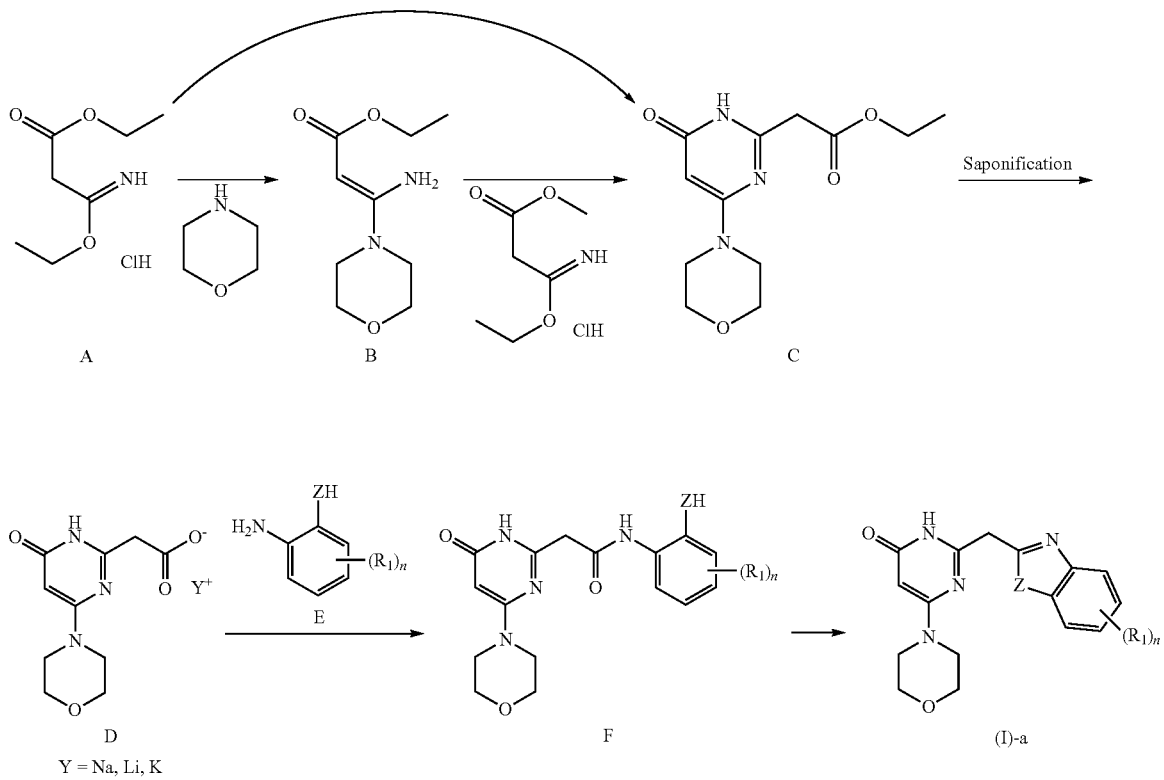

In General Scheme 1A, the substituents R1 and Z assume the values defined above, and in particular Z=NH and O.

The aminal ketene B can be obtained from the iminoether A or from the commercially available aminoacrylate tautomer thereof, by reaction with morpholine in a solvent such as ethanol, at a temperature of between 0° C. and the boiling point of the solvent, according to the process described by Landwehr J. et al. in J. Med. Chem. 2006, 49, 4327-4332.

The ester C can be obtained by reaction of the aminal ketene B with the iminoether A, or the aminoacrylate tautomer thereof, in a solvent such as ethanol, at a temperature of between 20° C. and the boiling point of the solvent. Alternatively, the ester C can be obtained by "one-pot" reaction between morpholine and an excess (for example, 3 equivalents) of iminoether A (or of aminoacrylate tautomer thereof) in a solvent such as ethanol, at a temperature of between 20° C. and the boiling point of the solvent.

The carboxylate D can be obtained by hydrolysis of the ester C in the presence of a base such as sodium hydroxide or lithium hydroxide, in a solvent such as tetrahydrofuran or methanol, at a temperature between 0° C. and 30° C.

The amides F can be obtained from the carboxylate D by condensation of an aniline E in the presence of a peptide coupling agent such as ethyldimethylaminopropyl carbodiimide (EDCI), 4-(4,6-dimethoxy-1,2,3-triazin-2-yl)-4-methylmorpholinium chloride (DMT-MM), benzotriazol-1-yloxytris(dimethylamino)phosphonium hexafluorophosphate (BOP), benzotriazol-1-yloxytrispyrrolidinophosphonium hexafluorophosphate (PyBOP), bromotrispyrrolidinophosphonium hexafluorophosphate (PyBROP), O-(7-azabenzotriazol-1-yl)-1,1,3,3-tetramethyluronium)hexafluorophosphate (HATU), or a hydroxybenzotriazole/ethyldimethylaminopropyl carbodiimide, HOBT/EDCI, mixture in a solvent such as dimethylformamide, pyridine, ethanol, water or methanol, at a temperature of between 20° C. and 50° C., for instance under the conditions described by Kunishima M. et al. in Tetrahedron 2001, 57, 1551-1558.

The products (I)-a can be obtained from the amides F by cyclodehydratation in a solvent such as acetic acid, or in the presence of an acid such as para-toluenesulphonic acid, in a solvent such as toluene, xylene or n-butanol, at the boiling point of the solvent, according to, for example, the process described by Arakawa. K et al. in Chemical and Pharmaceutical Bulletin, 45 (12), 1984-1993, 1997.

General Scheme 1B:

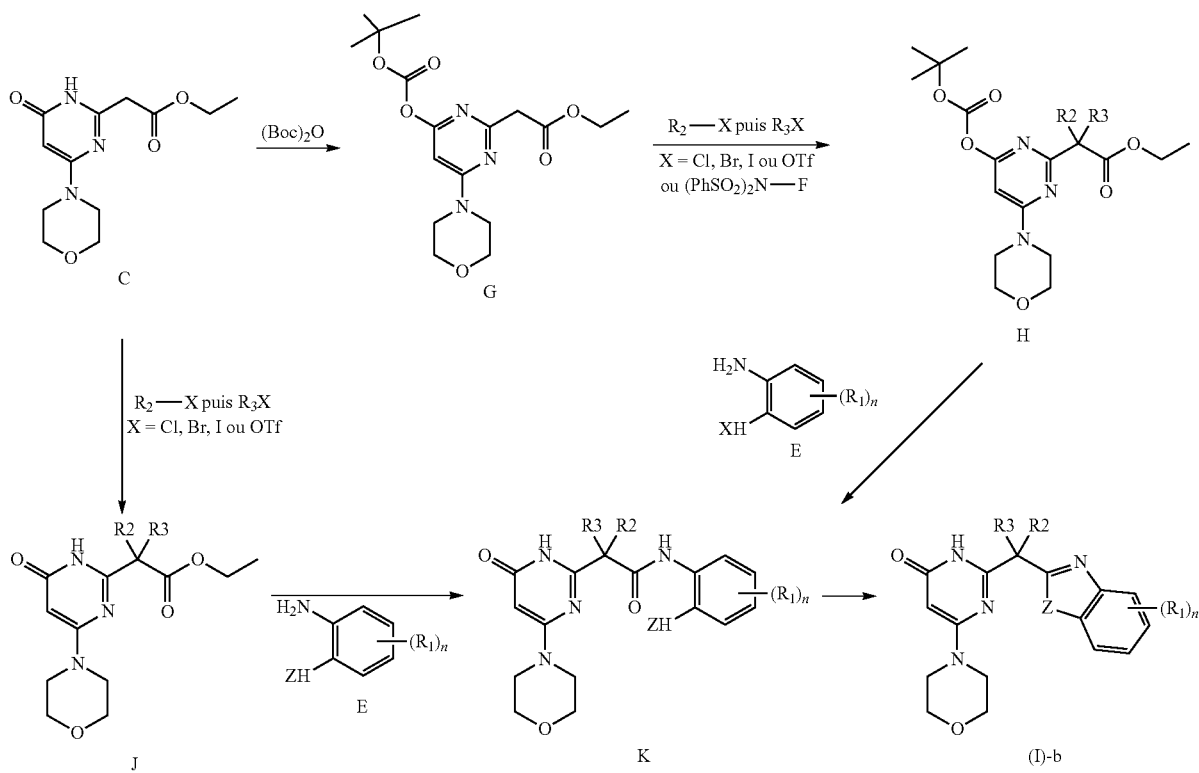

In General Scheme 1B, the substituents R1, R2, R3 and Z assume the values defined above, and in particular Z=NH and O.

The ester G can be obtained from the ester C by reaction with (Boc)₂O (tert-butyl dicarbonate), in a solvent such as dimethylformamide, dioxane, acetonitrile or dichloromethane, in the presence of a base such as for example, sodium hydride, triethylamine, N,N-diisopropylethylamine or pyridine, at a temperature of between 0° C. and 60° C., according to, for example, the process described by Hioki K. et al. Synthesis 2006, 12, 1931-1933.

The products H can be obtained from the ester G by reaction with R2-X, and then optionally, with R3-X (X=Cl, Br, I or OTf, and R2 and R3 are alkyl groups), in the presence of a base such as sodium hydroxide, potassium tert-butoxide or cesium carbonate, in a solvent such as methanol, ethanol or dioxane, at a temperature of between 0° C. and 100° C., according to, for example, the process described by Noël D. D'Angelo et al. in J. Med. Chem. 2008, 51, 5766-5779.

The product H where R2=R3=F can be obtained by reaction of the product G with the N-fluorobenzenesulphonimide, in the presence of a base such as the potassium salt of hexamethyldisilylazane, in a solvent such as tetrahydrofuran, at a temperature of between −78° C. and 20° C., according to, for example, the process described by Christopher S. Burgey et al. in J. Med. Chem. 2003, 46, 461-473.

The esters J where the R2 and R3 groups are alkyl radicals can be obtained from the ester C in the same way as the products H, in the presence of a base such as butyllithium, sodium hydride, potassium tert-butoxide or cesium carbonate in a solvent such as methanol, ethanol, tetrahydrofuran, dimethylformamide or dioxane, at a temperature of between 0° C. and 100° C.

The amides K can be obtained from the esters H or J, by reaction of an aniline E, in the presence of an agent such as trimethylaluminium, in a solvent such as toluene, at a temperature of between 20° C. and the boiling point of the solvent, for instance under the conditions described by Auzeloux, P et al. in J. Med. Chem. 2000, 43 (2), 190-197. The products (I)-b can be obtained from the amides K by cyclodehydratation, in the presence of an acid such as para-toluenesulphonic acid, in a solvent such as acetic acid, toluene, xylene or n-butanol, at the boiling point of the solvent, according to, for example, the process described by Arakawa K. et al., in Chemical and Pharmaceutical Bulletin (1997) 45 (12), 1984-1993.

Among the starting products of formula A or B, some are known and can be obtained either commercially, or according to the usual methods known to those skilled in the art, for example from commercially available products.

It is understood, for those skilled in the art, that, in order to implement the processes according to the invention, described above, it may be necessary to introduce protective groups for amino, carboxyl and alcohol functions in order to prevent side reactions.

The following non-exhaustive list of examples of protection of reactive functions may be mentioned:

hydroxyl groups can be protected, for example, with alkyl radicals such as tert-butyl, trimethylsilyl, tert-butyldimethylsilyl, methoxymethyl, tetrahydropyranyl, benzyl or acetyl, amino groups can be protected, for example, with acetyl, trityl, benzyl, tert-butoxycarbonyl, BOC, benzyloxycarbonyl or phthalimido radicals or other radicals known in peptide chemistry.

Acid functions can be protected, for example, in the form of esters formed with readily cleavable esters such as benzyl or tert-butyl esters, or esters known in peptide chemistry.

A list of various protective groups that can be used will be found in the manuals known to those skilled in the art, and for example in patent BF 2 499 995.

It may be noted that it is possible, if desired and if necessary, to subject intermediate products or products of formula (I) thus obtained by means of the processes indicated above, in order to obtain other intermediates or other products of formula (I), to one or more conversion reactions known to those skilled in the art, such as, for example:
a) a reaction for esterification of an acid function,
b) a reaction for saponification of an ester function to give an acid function,
c) a reaction for reduction of the free or esterified carboxyl function to give an alcohol function,
d) a reaction for conversion of an alkoxy function to give a hydroxyl function, or else of a hydroxyl function to give an alkoxy function,
e) a reaction for removal of the protective groups that the protected reactive functions may be carrying,
f) a reaction for salification with an inorganic or organic acid or with a base so as to obtain the corresponding salt,
g) a reaction for resolving the racemic forms to give resolved products, said products of formula (I) thus obtained being in all the possible racemic, enantiomeric and diastereoisomeric isomer forms.

The reactions a) to g) can be carried out under the usual conditions known to those skilled in the art, such as, for example, those indicated hereinafter.

a) The products described above may, if desired, be the subject, on the possible carboxyl functions, of esterification reactions which can be carried out according to the usual methods known to those skilled in the art.

b) The possible conversions of ester functions to give acid functions of the products described above may, if desired, be carried out under the usual conditions known to those skilled in the art, in particular by acid or alkaline hydrolysis, for example with sodium hydroxide or potassium hydroxide in an alcohol medium such as, for example, in methanol, or else with hydrochloric acid or sulphuric acid.

The saponification reaction can be carried out according to the usual methods known to those skilled in the art, such as, for example, in a solvent such as methanol or ethanol, dioxane or dimethoxyethane, in the presence of sodium hydroxide or of potassium hydroxide.

c) The possible free or esterified carboxyl functions of the products described above may, if desired, be reduced to give alcohol functions by means of the methods known to those skilled in the art: the possible esterified carboxyl functions may, if desired, be reduced to give alcohol functions by means of the methods known to those skilled in the art, and in particular with lithium aluminium hydride in a solvent such as, for example, tetrahydrofuran, or else dioxane or ethyl ether.

The possible free carboxyl functions of the products described above may, if desired, be reduced to give alcohol functions in particular with boron hydride.

d) The possible alkoxy functions, such as in particular methoxy functions, of the products described above may, if necessary, be converted to hydroxyl functions under the usual conditions known to those skilled in the art, for example with boron tribromide in a solvent such as, for example, methylene chloride, with pyridine hydrobromide or hydrochloride or else with hydrobromic acid or hydrochloric acid in water or trifluoroacetic acid at reflux.

e) The removal of protective groups such as, for example, those indicated above can be carried out under the usual conditions known to those skilled in the art, in particular by acid hydrolysis carried out with an acid such as hydrochloric acid, benzenesulphonic acid, para-toluenesulphonic acid, formic acid or trifluoroacetic acid, or else by catalytic hydrogenation.

The phthalimido group may be removed with hydrazine.

f) The products described above may, if desired, be the subject of salification reactions, for example with an inorganic or organic acid or with an inorganic or organic base, according to the usual methods known to those skilled in the art: such a salification reaction can be carried out, for example, in the presence of hydrochloric acid, or else of tartaric acid, citric acid or methanesulphonic acid, in an alcohol such as, for example, ethanol or methanol.

g) The possible optically active forms of the products described above can be prepared by resolving the racemic mixtures according to the usual methods known to those skilled in the art.

The products of formula (I) as defined above, and also the addition salts thereof with acids, have advantageous pharmacological properties, in particular due to their kinase-inhibiting properties, as is indicated above.

The products of the present invention are in particular of use in tumour therapy.

The products of the invention may also thus increase the therapeutic effects of commonly used antitumour agents.

These properties justify the use thereof in therapy, and a subject of the invention is in particular, as medicaments, the products of formula (I) as defined above, said products of formula (I) being in all the possible racemic, enantiomeric and diastereoisomeric isomer forms, and also the pharmaceutically acceptable addition salts with inorganic and organic acids or with inorganic and organic bases, of said products of formula (I).

A subject of the invention is most particularly as medicaments, the products corresponding to the following formulae:
2-[(5-fluoro-1H-benzimidazol-2-yl)methyl]-6-(morpholin-4-yl)pyrimidin-4(3H)-one
2-(1,3-benzoxazol-2-ylmethyl)-6-(morpholin-4-yl)pyrimidin-4(3H)-one
2-[(6-bromo-1H-benzimidazol-2-yl)methyl]-6-(morpholin-4-yl)pyrimidin-4(3H)-one
2-[(6-methoxy-1H-benzimidazol-2-yl)methyl]-6-(morpholin-4-yl)pyrimidin-4(3H)-one
2-[(5,6-difluoro-1H-benzimidazol-2-yl)methyl]-6-(morpholin-4-yl)pyrimidin-4(3H)-one
2-[(6-fluoro-1,3-benzoxazol-2-yl)methyl]-6-(morpholin-4-yl)pyrimidin-4(3H)-one
2-[(5-fluoro-1,3-benzoxazol-2-yl)methyl]-6-(morpholin-4-yl)pyrimidin-4(3H)-one
2-[(6-methyl-1,3-benzoxazol-2-yl)methyl]-6-(morpholin-4-yl)pyrimidin-4(3H)-one
2-[(6-bromo-1,3-benzoxazol-2-yl)methyl]-6-(morpholin-4-yl)pyrimidin-4(3H)-one
2-[(1-methyl-1H-benzimidazol-2-yl)methyl]-6-(morpholin-4-yl)pyrimidin-4(3H)-one
2-[(5-fluoro-1-methyl-1H-benzimidazol-2-yl)methyl]-6-(morpholin-4-yl)pyrimidin-4(3H)-one
2-[(7-fluoro-1,3-benzoxazol-2-yl)methyl]-6-(morpholin-4-yl)pyrimidin-4(3H)-one
6-(morpholin-4-yl)-2-[(1-phenyl-1H-benzimidazol-2-yl)methyl]pyrimidin-4(3H)-one
2-[(1-benzyl-1H-benzimidazol-2-yl)methyl]-6-(morpholin-4-yl)pyrimidin-4(3H)-one 2-[(1-ethyl-1H-benzimidazol-2-yl)methyl]-6-(morpholin-4-yl)pyrimidin-4(3H)-one
2-[(5,6-difluoro-1,3-benzoxazol-2-yl)methyl]-6-(morpholin-4-yl)pyrimidin-4(3H)-one
2-[(6-chloro-1H-benzimidazol-2-yl)methyl]-6-(morpholin-4-yl)pyrimidin-4(3H)-one
2-[(1-cyclopropyl-5-fluoro-1H-benzimidazol-2-yl)methyl]-6-(morpholin-4-yl)pyrimidin-4(3H)-one
2-{[5-fluoro-1-(2-methoxyethyl)-1H-benzimidazol-2-yl]methyl}-6-(morpholin-4-yl)pyrimidin-4(3H)-one
6-(morpholin-4-yl)-2-(naphtho[2,1-d][1,3]oxazol-2-ylmethyl)pyrimidin-4(3H)-one
2-[(6-methoxy-1,3-benzoxazol-2-yl)methyl]-6-(morpholin-4-yl)pyrimidin-4(3H)-one
2-[(6,7-difluoro-1,3-benzoxazol-2-yl)methyl]-6-(morpholin-4-yl)pyrimidin-4(3H)-one
2-[(5,6-dichloro-1H-benzimidazol-2-yl)methyl]-6-(morpholin-4-yl)pyrimidin-4(3H)-one
2-[(6-methyl-1H-benzimidazol-2-yl)methyl]-6-(morpholin-4-yl)pyrimidin-4(3H)-one
2-{[4-chloro-6-(trifluoromethyl)-1H-benzimidazol-2-yl]methyl}-6-(morpholin-4-yl)pyrimidin-4(3H)-one
6-(morpholin-4-yl)-2-{[6-(trifluoromethyl)-1H-benzimidazol-2-yl]methyl}pyrimidin-4(3H)-one
2-[(5-chloro-6-fluoro-1H-benzimidazol-2-yl)methyl]-6-(morpholin-4-yl)pyrimidin-4(3H)-one
2-[(6,7-difluoro-1H-benzimidazol-2-yl)methyl]-6-(morpholin-4-yl)pyrimidin-4(3H)-one
2-[(5-chloro-6-methyl-1H-benzimidazol-2-yl)methyl]-6-(morpholin-4-yl)pyrimidin-4(3H)-one
(2-{[4-(morpholin-4-yl)-6-oxo-1,6-dihydropyrimidin-2-yl]methyl}-1H-benzimidazol-1-yl)acetonitrile
2-[(5,7-difluoro-1H-benzimidazol-2-yl)methyl]-6-(morpholin-4-yl)pyrimidin-4(3H)-one
2-{[5-chloro-1-(1-phenylethyl)-1H-benzimidazol-2-yl]methyl}-6-(morpholin-4-yl)pyrimidin-4(3H)-one
2-[(1-cyclohexyl-1H-benzimidazol-2-yl)methyl]-6-(morpholin-4-yl)pyrimidin-4(3H)-one
6-(morpholin-4-yl)-2-[(5,6,7-trifluoro-1H-benzimidazol-2-yl)methyl]pyrimidin-4(3H)-one
2-[(4-bromo-6-fluoro-1H-benzimidazol-2-yl)methyl]-6-(morpholin-4-yl)pyrimidin-4(3H)-one
2-[(6-bromo-1-methyl-1H-benzimidazol-2-yl)methyl]-6-(morpholin-4-yl)pyrimidin-4(3H)-one
2-[(6,7-difluoro-1-methyl-1H-benzimidazol-2-yl)methyl]-6-(morpholin-4-yl)pyrimidin-4(3H)-one
2-[(5,6-dichloro-1-methyl-1H-benzimidazol-2-yl)methyl]-6-(morpholin-4-yl)pyrimidin-4(3H)-one
6-(morpholin-4-yl)-2-[(5,6,7-trifluoro-1-methyl-1H-benzimidazol-2-yl)methyl]pyrimidin-4(3H)-one
2-[(4-hydroxy-1,3-benzoxazol-2-yl)methyl]-6-(morpholin-4-yl)pyrimidin-4(3H)-one
2-[(7-bromo-1-methyl-1H-benzimidazol-2-yl)methyl]-6-(morpholin-4-yl)pyrimidin-4(3H)-one
and also the pharmaceutically acceptable addition salts with inorganic and organic acids or with inorganic and organic bases, of said products of formula (I).

The invention also relates to pharmaceutical compositions containing, as active ingredient, at least one of the products of formula (I) as defined above or a pharmaceutically acceptable salt of this product or a prodrug of this product, and, where appropriate, a pharmaceutically acceptable carrier.

The invention thus extends to the pharmaceutically acceptable compositions containing, as active ingredient, at least one of the medicaments as defined above.

Such pharmaceutical compositions of the present invention may also, where appropriate, contain active ingredients of other antimitotic medicaments, such as in particular those based on taxol, cis-platin, DNA-intercalating agents, and the like.

These pharmaceutical compositions may be administered orally, parenterally, or locally by topical application to the skin and the mucous membranes, or by intravenous or intramuscular injection.

These compositions may be solid or liquid and may be in all the pharmaceutical forms commonly used in human medicine, for instance simple or sugar-coated tablets, pills, lozenges, gel capsules, drops, granules, injectable preparations, ointments, creams or gels; they are prepared according to the usual methods. The active ingredient may be incorporated therein in excipients normally used in these pharmaceutical compositions, such as talc, gum arabic, lactose, starch, magnesium stearate, cocoa butter, aqueous or nonaqueous carriers, the fatty substances of animal or plant origin, paraffin derivatives, glycols, various wetting agents, dispersants or emulsifiers, or preservatives.

The usual dosage, which is variable depending on the product used, the individual treated and the condition in question, may, for example, be from 0.05 to 5 g per day in adults or preferably from 0.1 to 2 g per day.

Such a medicament may in particular be for use in the treatment or prevention of a disease in a mammal.

A subject of the present invention is in particular the use of a product of formula (I) as defined above for the preparation of a medicament for use in the prevention or treatment of diseases associated with an uncontrolled proliferation.

A subject of the present invention is thus most particularly the use of a product of formula (I) as defined above, for the preparation of a medicament for use in the treatment or prevention of diseases in oncology and in particular for use in the treatment of cancers.

Among these cancers, the focus is on the treatment of solid or liquid tumours and on the treatment of cancers resistant to cytotoxic agents.

The cited products of the present invention may especially be used in the treatment of primary tumours and/or of metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid hematapoietic tumours, in sarcomas, in brain, larynx and lymphatic system cancers, bone and pancreatic cancers, and in hamartomas.

A subject of the present invention is also the use of the products of formula (I) as defined above for the preparation of medicaments for use in cancer chemotherapy.

A subject of the present invention is thus the products of formula (I) as defined above, for the use thereof in the treatment of cancers.

A subject of the present invention is the products of formula (I) as defined above, for the use thereof in the treatment of solid or liquid tumours.

A subject of the present invention is therefore the products of formula (I) as defined above, for the use thereof in the treatment of cancers resistant to cytotoxic agents.

A subject of the present invention is therefore the products of formula (I) as defined above, for the use thereof in the treatment of primary tumours and/or of metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid hematapoietic tumours, in sarcomas, in brain, larynx and lymphatic system cancers, bone and pancreatic cancers, and in hamartomas.

A subject of the present invention is therefore the products of formula (I) as defined above, for the use thereof in cancer chemotherapy.

Such medicaments for use in cancer chemotherapy may be used alone or in combination.

A subject of the present invention is therefore the products of formula (I) as defined above, for the use thereof in cancer chemotherapy, alone or in combination.

The products of the present application may in particular be administered alone or in combination with chemotherapy or radiotherapy or else in combination, for example, with other therapeutic agents.

Such therapeutic agents may be commonly used antitumour agents.

A subject of the present invention is also, as novel industrial products, the synthesis intermediates of formulae C, D, F, J and K as defined above and recalled below:

C
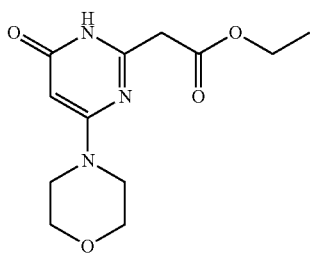 [SMILES: CCOC(=O)Cc1nc(N2CCOCC2)cc(=O)[nH]1]

D
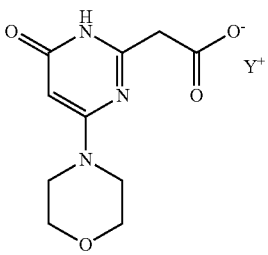

Y = Na, Li, K

F
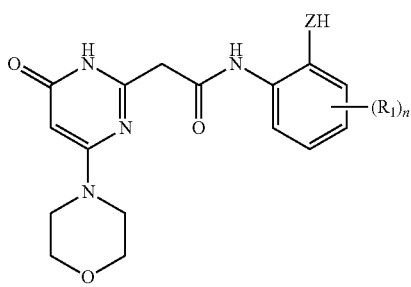

J
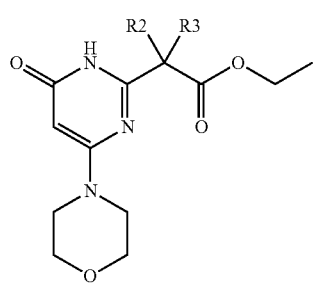

K
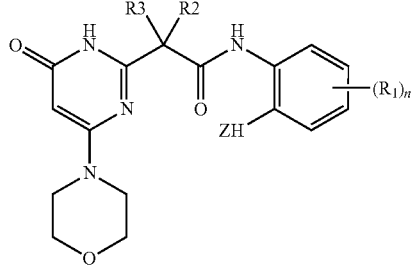

X = NH, O in which R1, R2, R3 and Z have the meaning indicated in either one of claims 1 and 2. The following examples, which are products of formula (I) illustrate the invention without, however, limiting it.

EXPERIMENTAL SECTION

The nomenclature of the compounds of this present invention was carried out with the ACDLABS software, Version 10.0.

The microwave oven used is a Biotage, Initiator™ 2.0, 400 W max, 2450 MHz instrument.

The $^1$H NMR spectra at 400 MHz and the $^1$H NMR spectra at 500 MHz were performed on a Bruker Avance DRX-400 or Bruker Avance DPX-500 spectrometer with the chemical shifts (δ in ppm) in the solvent dimethylsulphoxide-$d_6$ ($d_6$-DMSO) referenced at 2.5 ppm at a temperature of 303 K.

The mass spectra (MS) were obtained either by method A, method B or by method C:

Method A:

Waters UPLC-SQD instrument; ionization: positive and/or negative mode electrospray (ES+/−); chromatographic conditions: column: Acquity BEH $C_{18}$ 1.7 μm-2.1×50 mm; solvents: A: $H_2O$ (0.1% formic acid) B: $CH_3CN$ (0.1% formic acid); column temperature: 50° C.; flow rate: 1 ml/min; gradient (2 min): from 5% to 50% of B in 0.8 min; 1.2 min: 100% of B; 1.85 min: 100% of B; 1.95:5% of B; retention time=Tr (min).

Method B:

Waters ZQ instrument; ionization: positive and/or negative mode electrospray (ES+/−); chromatographic conditions: column: XBridge $C_{18}$ 2.5 μm-3×50 mm; solvents: A: $H_2O$ (0.1% formic acid) B: $CH_3CN$ (0.1% formic acid); column temperature: 70° C.; flow rate: 0.9 ml/min; gradient (7 min): from 5% to 100% of B in 5.3 min; 5.5 min: 100% of B; 6.3 min: 5% of B; retention time=Tr (min).

Method C:

Waters UPLC instrument, BEH C18 column, 2.1×50 mm; 1.7 u, $H_2O$+0.1% TFA:AcN+0.08% TFA 95:5 (0 min) to 5:95 (1.1 min) to 5:95 (1.7 min) to 95:5 (1.8 min) to 95:5 (2 min), 0.9 ml/min 55° C.; Waters SQD Single Quadrupol, 0.5 s scan time for mass 120-1200.

Example 1

Synthesis of 2-[4-(morpholin-4-yl)-6-oxo-1,6-dihydropyrimidin-2-yl]-N-phenylacetamide Stage 1

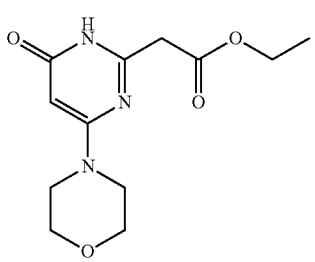

168.5 ml of ethyl 3-ethoxy-3-iminopropanoate hydrochloride, and then 155 ml of N,N-diisopropylethylamine in 200 ml of ethanol are added to a solution of 25 g of morpholine in 400 ml of ethanol heated to 95° C. The reaction mixture is heated at 95° C. for 30 hours and then allowed to return to ambient temperature. The precipitate formed is filtered off through sintered glass and then washed with 100 ml of ethanol, twice 500 ml of water and, finally 500 ml of ethyl ether. The solid is dried under vacuum so as to give 35 g of ethyl[4-(morpholin-4-yl)-6-oxo-1,6-dihydropyrimidin-2-yl]acetate in the form of a white solid the characteristics of which are the following:

$^1$H NMR Spectrum (400 MHz, δ in ppm, $d_6$-DMSO): 1.19 (t, J=7.1 Hz, 3H); 3.38 to 3.44 (m, 4H); 3.56 (s, 2H); 3.61 (dd, J=4.0 and 5.7 Hz, 4H); 4.12 (q, J=7.1 Hz, 2H); 5.20 (s, 1H); 11.69 (broad s, 1H)

Mass spectrometry: Method A
Retention time Tr (min)=0.48;
[M+H]+: m/z 268; [M−H]−: m/z 266
Purity: 98%

Stage 2

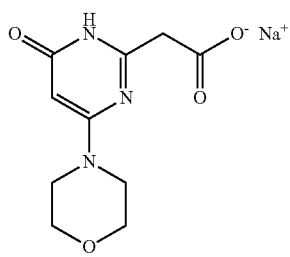 [SMILES: O=C([O-])Cc1nc(N2CCOCC2)cc(=O)[nH]1 ; [Na+]]

18.7 ml of 2M sodium hydroxide are added to a solution of 10 g of ethyl [4-(morpholin-4-yl)-6-oxo-1,6-dihydropyrimidin-2-yl]acetate in 300 ml of tetrahydrofuran. The reaction mixture is stirred for 48 hours at ambient temperature. The precipitate formed is filtered off through sintered glass, washed with ethyl acetate and rinsed several times with ethyl ether. The solid obtained is then dried in a rotary evaporator so as to give 8.7 g of sodium [4-(morpholin-4-yl)-6-oxo-1,6-dihydropyrimidin-2-yl]acetate in the form of a white solid, the characteristics of which are the following:

$^1$H NMR Spectrum (400 MHz, δ in ppm, $d_6$-DMSO): 3.08 (s, 2H); 3.38 (t, J=4.6 Hz, 4H); 3.61 (t, J=4.6 Hz, 4H); 5.08 (s, 1H); 13.16 (broad s, 1H)

Mass spectrometry: Method A
Retention time Tr (min)=0.29;
[M+H]+: m/z 240; [M−H]−: m/z 238
Purity: 98%

Stage 3:

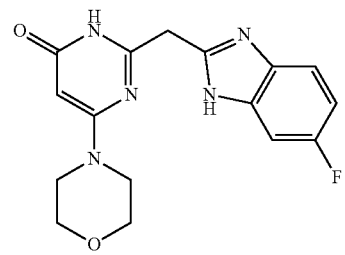 [SMILES: O=c1cc(N2CCOCC2)nc(Cc2nc3ccc(F)cc3[nH]2)[nH]1]

151 mg of 1,2-diamino-4-fluorobenzene are added to a solution of 261 mg of sodium [4-(morpholin-4-yl)-6-oxo-1,6-dihydropyrimidin-2-yl]acetate in 8 ml of methanol. The resulting mixture is stirred at ambient temperature for 5 minutes and then 354 mg of 4-(4,6-dimethoxy-1,3,5-triazin-2-yl)-4-methylmorpholin-4-ium chloride hydrate are added. The resulting mixture is thus stirred for 30 minutes at ambient temperature. The reaction mixture is then concentrated to dryness under reduced pressure, and the residue is then taken up in 30 ml of acetic acid. The reaction mixture is brought to reflux for 1 hour, and then concentrated under reduced pressure. 30 ml of water are then added and a saturated aqueous solution of sodium bicarbonate is added until a pH in the region of 7 is obtained. 20 ml of ethyl acetate are then added and the resulting mixture is stirred for 1 hour. The precipitate formed is filtered off and subsequently purified by silica gel column chromatography, elution being carried out with a gradient of the eluent $CH_2Cl_2$/MeOH: 80/20 in dichloromethane of 0% to 100% in 25 minutes. 140 mg of 2-[(5-fluoro-1H-benzimidazol-2-yl)methyl]-6-(morpholin-4-yl)pyrimidin-4(3H)-one are obtained in the form of an off-white solid, the characteristics of which are the following:

$^1$H NMR Spectrum (400 MHz, δ in ppm, $d_6$-DMSO): 3.37 (t, J=4.9 Hz, 4H); 3.58 (t, J=4.9 Hz, 4H); 4.08 (s, 2H); 5.22 (s, 1H); 7.00 (t, J=8.2 Hz, 1H); 7.31 (dd, J=0.7 and 9.8 Hz, 1H); 7.49 (broad s, 1H); 12.15 (broad s, 2H).

Mass spectrometry: Method A
Retention time Tr (min)=0.41;
[M+H]+: m/z 330; [M−H]−: m/z 328
Purity: 98%

Example 2

Synthesis of 2-(1,3-benzoxazol-2-ylmethyl)-6-(morpholin-4-yl)pyrimidin-4(3H)-one

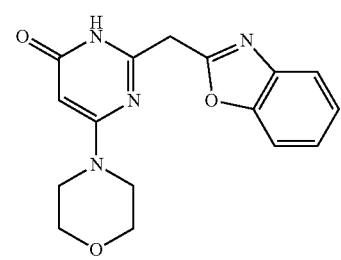 [SMILES: O=c1cc(N2CCOCC2)nc(Cc2nc3ccccc3o2)[nH]1]

Stage 1

4 ml of pyridine, 550 mg of N-[3-(dimethylamino)propyl]-N'-ethylcarbodiimide hydrochloride and 700 mg of 2-aminophenol are added to a solution of 500 mg of sodium [4-(morpholin-4-yl)-6-oxo-1,6-dihydropyrimidin-2-yl]acetate in 4 ml of dimethylformamide. The reaction mixture is stirred at ambient temperature overnight, and is then concentrated under reduced pressure. Water and ethyl acetate are added and the resulting mixture is thus stirred for 30 minutes. The precipitate formed is filtered off, and rinsed with water, ethyl ether and petroleum ether. The solid obtained is dried under vacuum. 370 mg of N-(2-hydroxyphenyl)-2-[4-(morpholin-4-yl)-6-oxo-1,6-dihydropyrimidin-2-yl]acetamide are thus obtained in the form of a beige solid, the characteristics of which are the following:

Mass spectrometry: Method B
Retention time Tr (min)=2.58;
[M+H]+: m/z 331; [M−H]−: m/z 329
Purity: 98%

Stage 2

20 mg of 4-methylbenzenesulphonic acid hydrate are added to a solution of 200 mg of N-(2-hydroxyphenyl)-2-[4-(morpholin-4-yl)-6-oxo-1,6-dihydropyrimidin-2-yl]acetamide in 40 ml of toluene. The reaction mixture is brought to reflux overnight. After cooling to 0° C., the insoluble material formed is filtered off. The filtrate is concentrated to dryness under reduced pressure and the residue is then chromatographed on a silica gel column, eluent: CH$_2$Cl$_2$/MeOH: 98/02 then 90/10. 16 mg of 2-(1,3-benzoxazol-2-ylmethyl)-6-(morpholin-4-yl)pyrimidin-4(3H)-one are thus obtained in the form of a white solid, the characteristics of which are the following:

$^1$H NMR Spectrum (400 MHz, δ in ppm, d$_6$-DMSO): 3.35 (t, J=5.0 Hz, 4H); 3.56 (t, J=4.9 Hz, 4H); 4.25 (s, 2H); 5.25 (broad s, 1H); 7.31 to 7.40 (m, 2H); 7.62 to 7.74 (m, 2H); 11.92 (broad s, 1H).

Mass spectrometry: Method A
Retention time Tr (min)=0.60
[M+H]+: m/z 313; [M−H]−: m/z 311
Purity: 98%
Melting point (Köfler bench)=224° C.

Example 3

Synthesis of 2-[(5-bromo-1H-benzimidazol-2-yl)methyl]-6-(morpholin-4-yl)pyrimidin-4(3H)-one

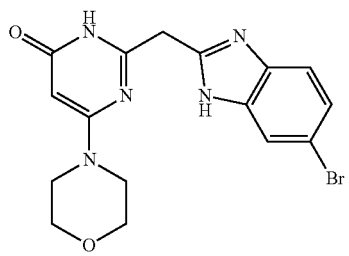 [SMILES: O=c1cc(N2CCOCC2)nc(Cc2nc3ccc(Br)cc3[nH]2)[nH]1]

In a round-bottomed flask, 1.3 g of sodium [4-(morpholin-4-yl)-6-oxo-1,6-dihydropyrimidin-2-yl]acetate are introduced into 10 ml of dimethylformamide and then 10 ml of pyridine, 1.44 g of N-[3-(dimethylamino)propyl]-N'-ethylcarbodiimide hydrochloride and 1.87 g of 4-bromobenzene-1,2-diamine are added. The reaction mixture is stirred at ambient temperature overnight and is then concentrated to dryness under reduced pressure. The residue is taken up in 40 ml of acetic acid and brought to reflux for 4 hours, then concentrated under reduced pressure. 100 ml of water are then added and a saturated aqueous solution of sodium bicarbonate is added until a pH in the region of 7 is obtained. 200 ml of ethyl acetate are then added and the resulting mixture is stirred for 1 hour. The precipitate formed is filtered then purified by silica gel column chromatography, elution being carried out with a gradient of the eluent CH$_2$Cl$_2$/MeOH: 80/20 in dichloromethane of 0% to 100% in 25 minutes. 560 mg of 2-[(5-bromo-1H-benzimidazol-2-yl)methyl]-6-(morpholin-4-yl)pyrimidin-4(3H)-one are obtained in the form of an off-white solid, the characteristics of which are the following:

$^1$H NMR Spectrum (400 MHz): 3.34 to 3.39 (m, 4H); 3.55 to 3.59 (m, 4H); 4.09 (s, 2H); 5.21 (s, 1H); 7.28 (dd, J=2.0 and 8.6 Hz, 1H); 7.47 (d, J=8.6 Hz, 1H); 7.71 (d, J=2.0 Hz, 1H); 12.20 (broad m, 2H).

Mass spectrometry: Method B
Retention time Tr (min)=2.71;
[M+H]+: m/z 390; [M−H]−: m/z 388
Purity: 98%

Example 4

Synthesis of 2-[(6-methoxy-1H-benzimidazol-2-yl)methyl]-6-(morpholin-4-yl)pyrimidin-4(3H)-one

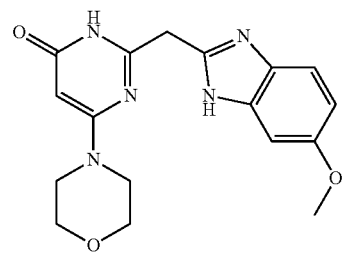 [SMILES: COc1ccc2nc(Cc3nc(N4CCOCC4)cc(=O)[nH]3)[nH]c2c1]

The product is prepared according to the procedure described in Stage 3 of Example 1, using 261 mg of sodium [4-(morpholin-4-yl)-6-oxo-1,6-dihydropyrimidin-2-yl]acetate and 166 mg of 1,2-diamino-4-methoxybenzene in place of the 1,2-diamino-4-fluorobenzene. After purification by silica gel column chromatography, elution being carried out with a gradient of pure CH$_2$Cl$_2$ to CH$_2$Cl$_2$/MeOH: 85/15, 8 mg of 2-[(6-methoxy-1H-benzimidazol-2-yl)methyl]-6-(morpholin-4-yl)pyrimidin-4(3H)-one being obtained in the form of an off-white solid, the characteristics of which are the following:

$^1$H NMR Spectrum (400 MHz): 3.38 (m, 4H); 3.58 (m, 4H); 3.76 (s, 3H); 4.04 (s, 2H); 5.21 (s, 1H); 6.72 to 6.82 (m, 1H); 6.89 to 7.15 (broad m, 1H); 7.27 to 7.52 (broad m, 1H); 11.82 (broad m, 1H); 12.11 (broad m, 1H).

Mass spectrometry: Method A
Retention time Tr (min)=0.40;
[M+H]+: m/z 342
Purity: 90%

Example 5

Synthesis of 2-[(5,6-difluoro-1H-benzimidazol-2-yl)methyl]-6-(morpholin-4-yl)pyrimidin-4(3H)-one

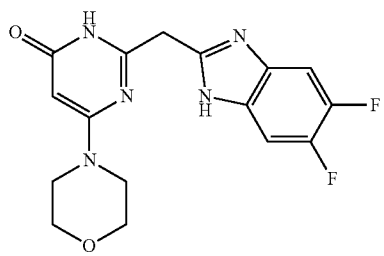 [SMILES: O=c1cc(N2CCOCC2)nc(Cc2nc3cc(F)c(F)cc3[nH]2)[nH]1]

The product is prepared according to the procedure described in Stage 3 of Example 1, using 261 mg of sodium [4-(morpholin-4-yl)-6-oxo-1,6-dihydropyrimidin-2-yl]acetate and 173 mg of 1,2-diamino-4,5-difluorobenzene in place of the 1,2-diamino-4-fluorobenzene. After purification by silica gel column chromatography, elution being carried out with a gradient of pure $CH_2Cl_2$ to $CH_2Cl_2$/MeOH: 85/15, 150 mg of 2-[(5,6-difluoro-1H-benzimidazol-2-yl)methyl]-6-(morpholin-4-yl)pyrimidin-4(3H)-one are obtained in the form of a light pink solid, the characteristics of which are the following:

$^1$H NMR Spectrum (400 MHz): 3.34 to 3.39 (m, 4H); 3.55 to 3.60 (m, 4H); 4.08 (s, 2H); 5.21 (s, 1H); 7.57 (dd, J=7.8 and 10.8 Hz, 2H); 12.16 (broad s, 2H).

Mass spectrometry: Method A

Retention time Tr (min)=0.51;

[M+H]+: m/z 348; [M−H]−: m/z 346

Purity: 98%

Example 6

Synthesis of 2-[(6-fluoro-1,3-benzoxazol-2-yl)methyl]-6-(morpholin-4-yl)pyrimidin-4(3H)-one

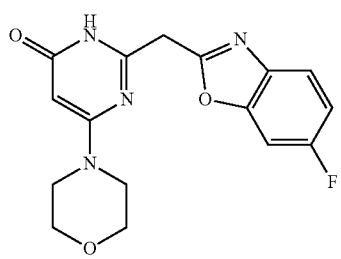 [SMILES: O=c1cc(N2CCOCC2)nc(Cc2nc3ccc(F)cc3o2)[nH]1]

Stage 1

The product is prepared according to the procedure described in Stage 1 of Example 2, using 550 mg of sodium [4-(morpholin-4-yl)-6-oxo-1,6-dihydropyrimidin-2-yl]acetate and 815 mg of 2-amino-5-fluorophenol in place of 2-aminophenol. After purification by silica gel column chromatography, elution being carried out with pure $CH_2Cl_2$ then $CH_2Cl_2$/MeOH: 95/05, 149 mg of N-(4-fluoro-2-hydroxyphenyl)-2-[4-(morpholin-4-yl)-6-oxo-1,6-dihydropyrimidin-2-yl]acetamide obtained in the form of a grey solid, the characteristics of which are the following:

Mass spectrometry: Method B

Retention time Tr (min)=2.74;

[M+H]+: m/z 349; [M−H]−: m/z 347

Stage 2:

The product is prepared according to the procedure described in Stage 2 of Example 2, using 120 mg of N-(4-fluoro-2-hydroxyphenyl)-2-[4-(morpholin-4-yl)-6-oxo-1,6-dihydropyrimidin-2-yl]acetamide, and 11 mg of 4-methylbenzenesulphonic acid hydrate, and replacing the toluene with xylene. After purification by silica gel column chromatography, eluent: $CH_2Cl_2$/MeOH: 98/02, 15 mg of 2-[(6-fluoro-1,3-benzoxazol-2-yl)methyl]-6-(morpholin-4-yl)pyrimidin-4(3H)-one are obtained in the form of a white solid, the characteristics of which are the following:

$^1$H NMR Spectrum (400 MHz): 3.35 (m, 4H); 3.56 (m, 4H); 4.25 (s, 2H); 5.25 (broad s, 1H); 7.24 (ddd, J=2.6 and 8.7 and 10.0 Hz, 1H); 7.70 to 7.77 (m, 2H); 11.93 (broad s, 1H)

Mass spectrometry: method A

Retention time Tr (min)=0.65

[M+H]+: m/z 329; [M−H]−: m/z 331

Example 7

Synthesis of 2-[(5-fluoro-1,3-benzoxazol-2-yl)methyl]-6-(morpholin-4-yl)pyrimidin-4(3H)-one

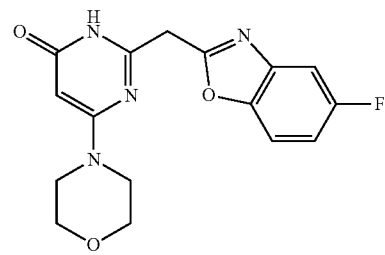 [SMILES: O=c1cc(N2CCOCC2)nc(Cc2nc3cc(F)ccc3o2)[nH]1]

Stage 1:

The product is prepared according to the procedure described in Stage 1 of Example 2, using 1 g of sodium [4-(morpholin-4-yl)-6-oxo-1,6-dihydropyrimidin-2-yl]acetate and 466 mg of 2-amino-4-fluorophenol in place of the 2,4-difluoroaniline. 795 mg of N-(5-fluoro-2-hydroxyphenyl)-2-[4-(morpholin-4-yl)-6-oxo-1,6-dihydropyrimidin-2-yl]acetamide are obtained in the form of a brown solid, the characteristics of which are the following:

Mass spectrometry: Method A

Retention time Tr (min)=0.55;

[M+H]+: m/z 349; [M−H]−: m/z 347

Purity: 98%

Stage 2:

The product is prepared according to the procedure described in Stage 2 of Example 2, using 700 mg of N-(5-fluoro-2-hydroxyphenyl)-2-[4-(morpholin-4-yl)-6-oxo-1,6-dihydropyrimidin-2-yl]acetamide and 292 mg of 4-methylbenzenesulphonic acid hydrate, and replacing the toluene with xylene. After purification by silica gel column chromatography, elution being carried out with a mixture of $CH_2Cl_2$/MeOH: 98/02, then $CH_2Cl_2$/MeOH: 95/05, followed by recrystallization from methanol, 188 mg of 2-[(5-fluoro-1,3-benzoxazol-2-yl)methyl]-6-(morpholin-4-yl)pyrimidin-4(3H)-one are obtained in the form of a brown solid, the characteristics of which are the following:

¹H NMR Spectrum (400 MHz): for this batch, all the signals are broad, with: 3.33 to 3.39 (m, 4H); 3.54 to 3.62 (m, 4H); 4.26 (s, 2H); 5.25 (s, 1H); 7.25 (t, J=9.0 Hz, 1H); 7.61 (d, J=9.0 Hz, 1H); 7.76 (dd, J=4.5 and 9.0 Hz, 1H); 11.83 to 11.96 (broad m, 1H)

Mass spectrometry: Method A
Retention time Tr (min)=0.65
[M+H]+: m/z 331; [M–H]–: m/z 329

Example 8

Synthesis of 2-[(6-methyl-1,3-benzoxazol-2-yl)methyl]-6-(morpholin-4-yl)pyrimidin-4(3H)one Stage 1:

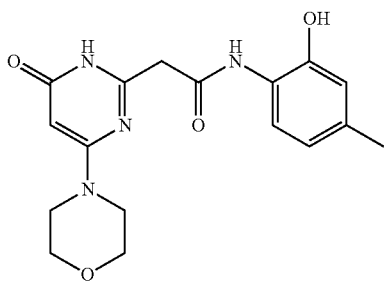 [SMILES: Cc1ccc(NC(=O)Cc2nc(N3CCOCC3)cc(=O)[nH]2)c(O)c1]

The product is prepared according to the procedure described in Example 2, using 500 mg of sodium [4-(morpholin-4-yl)-6-oxo-1,6-dihydropyrimidin-2-yl]acetate and 466 mg of 2-amino-5-methylphenol in place of the 2,4-difluoroaniline. 515 mg of N-(2-hydroxy-4-methylphenyl)-2-[4-(morpholin-4-yl)-6-oxo-1,6-dihydropyrimidin-2-yl]acetamide are obtained in the form of a purplish solid, the characteristics of which are the following:

Mass spectrometry: Method A
Retention time Tr (min)=0.57
[M+H]+: m/z 345; [M–H]–: m/z 343

Stage 2:

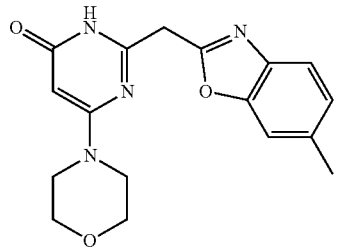 [SMILES: Cc1ccc2nc(Cc3nc(N4CCOCC4)cc(=O)[nH]3)oc2c1]

The product is prepared according to the procedure described in Example 2, using 390 mg of N-(2-hydroxy-4-methylphenyl)-2-[4-(morpholin-4-yl)-6-oxo-1,6-dihydropyrimidin-2-yl]acetamide and 108 mg of 4-methylbenzenesulphonic acid hydrate, and replacing the toluene with xylene. After recrystallization from 20 ml of ethanol and 5 ml of methanol, 105 mg of 2-[(6-methyl-1,3-benzoxazol-2-yl)methyl]-6-(morpholin-4-yl)pyrimidin-4(3H)-one are obtained in the form of a white solid, the characteristics of which are the following:

¹H NMR Spectrum (400 MHz): 2.43 (s, 3H); 3.36 (m, 4H); 3.56 (m, 4H); 4.21 (s, 2H); 5.24 (broad m, 1H); 7.18 (broad d, J=8.3Hz, 1H); 7.51 (broad s, 1H); 7.57 (d, J=8.3Hz, 1H); 11.91 (broad m, 1H)

Mass spectrometry: Method A
Retention time Tr (min)=0.69
[M+H]+: m/z 327; [M–H]–: m/z 325

Example 9

Synthesis of 2-[(6-bromo-1,3-benzoxazol-2-yl)methyl]-6-(morpholin-4-yl)pyrimidin-4(3H)-one Stage 1:

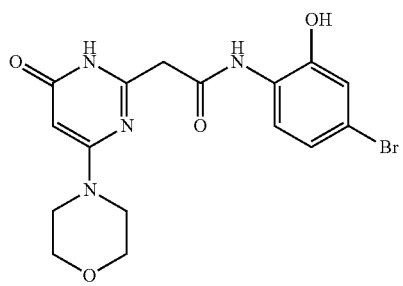 [SMILES: O=C(Cc1nc(N2CCOCC2)cc(=O)[nH]1)Nc1ccc(Br)cc1O]

The product is prepared according to the procedure described in Example 2, using 500 mg of sodium [4-(morpholin-4-yl)-6-oxo-1,6-dihydropyrimidin-2-yl]acetate and 520 mg of 2-amino-4-bromophenol in place of the 2,4-difluoroaniline. 350 mg of N-(4-bromo-2-hydroxyphenyl)-2-[4-(morpholin-4-yl)-6-oxo-1,6-dihydropyrimidin-2-yl]acetamide are obtained in the form of a purplish solid, the characteristics of which are the following:

Mass spectrometry: Method A
Retention time Tr (min)=0.65
[M+H]+: m/z 409; [M–H]–: m/z 407

Stage 2:

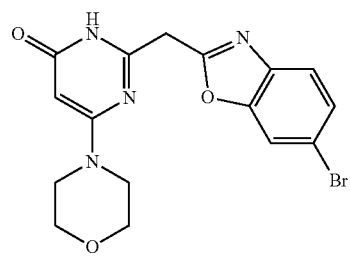

The product is prepared according to the procedure described in Example 2, using 316 mg of N-(4-bromo-2-hydroxyphenyl)-2-[4-(morpholin-4-yl)-6-oxo-1,6-dihydropyrimidin-2-yl]acetamide and 73 mg of 4-methylbenzenesulphonic acid hydrate, and replacing the toluene with xylene. After recrystallization from 30 ml of ethanol, 5 ml of methanol and 5 ml of dichloromethane and then purification of the formed precipitate by silica column chromatography, eluent: CH₂Cl₂/MeOH: 90/10, 70 mg of 2-[(6-bromo-1,3-benzoxazol-2-yl)methyl]-6-(morpholin-4-yl)pyrimidin-4(3H)-one are obtained in the form of an off-white solid, the characteristics of which are the following:

¹H NMR Spectrum: (400 MHz): 3.35 (m, 4H); 3.56 (m, 4H); 4.26 (s, 2H); 5.25 (broad m, 1H); 7.54 (dd, J=1.8 and 8.4 Hz, 1H); 7.69 (d, J=8.4 Hz, 1H); 8.07 (d, J=1.8 Hz, 1H); 11.92 (broad m, 1H)

Mass spectrometry: Method B
Retention time Tr (min)=3.40
[M+H]+: m/z 391; [M–H]–: m/z 389

Example 10

Synthesis of 2-[(1-methyl-1H-benzimidazol-2-yl)methyl]-6-(morpholin-4-yl)pyrimidin-4(3H)-one

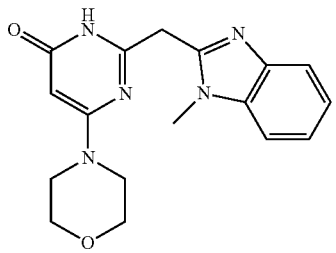 [SMILES: Cn1c(Cc2nc(N3CCOCC3)cc(=O)[nH]2)nc2ccccc21]

The product is prepared according to the procedure described in Example 3, using 300 mg of sodium [4-(morpholin-4-yl)-6-oxo-1,6-dihydropyrimidin-2-yl]acetate and 280 mg of N-methyl-1,2-phenylenediamine in place of the 4-bromobenzene-1,2-diamine. After purification by silica column chromatography, eluent: a gradient of the pure $CH_2Cl_2$ eluent to $CH_2Cl_2$/MeOH: 90/10, 225 mg of 2-[(1-methyl-1H-benzimidazol-2-yl)methyl]-6-(morpholin-4-yl)pyrimidin-4(3H)-one are obtained in the form of a white solid, the characteristics of which are the following:

$^1$H NMR Spectrum (400 MHz): 3.34 (m, 4H); 3.56 (m, 4H); 3.80 (s, 3H); 4.20 (s, 2H); 5.21 (s, 1H); 7.17 (t, J=7.8 Hz, 1H); 7.23 (t, J=7.8 Hz, 1H); 7.52 (d, J=7.8 Hz, 1H); 7.56 (d, J=7.8 Hz, 1H); 11.85 (broad s, 1H)

Mass spectrometry: Method A
Retention time Tr (min)=0.36
[M+H]+: m/z 326; [M−H]−: m/z 324

Example 11

Synthesis of 2-[(5-fluoro-1-methyl-1H-benzimidazol-2-yl)methyl]-6-(morpholin-4-yl)pyrimidin-4(3H)-one

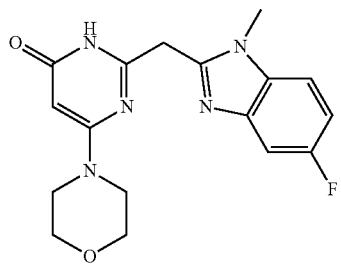 [SMILES: Cn1c(Cc2nc(N3CCOCC3)cc(=O)[nH]2)nc2cc(F)ccc21]

Stage 1:

0.75 ml of sodium hydroxide (2N) is added to a solution of 329 mg of 2-[(6-fluoro-1H-benzimidazol-2-yl)methyl]-6-(morpholin-4-yl)pyrimidin-4(3H)-one (Example 1, stage 3) in 15 ml of acetone. After stirring for ten minutes at a temperature in the region of 20° C., 0.93 ml of iodomethane is added. After a period overnight, the acetone is evaporated off, the residue is diluted in 20 ml of water, and the medium is brought to pH 6 using hydrochloric acid (2N). After the insoluble material has been filtered off, the filtrate is evaporated to dryness under reduced pressure and purified by silica column chromatography, eluent: $CH_2Cl_2$/MeOH: 95/05. 145 mg of a mixture of isomers are obtained, said mixture containing 50% of 2-[(5-fluoro-1-methyl-1H-benzimidazol-2-yl)methyl]-6-(morpholin-4-yl)pyrimidin-4(3H)-one which is purified in the next stage:

Mass spectrometry: Method A
Retention time Tr (min)=0.43 and 0.45:50-50 mixture of isomers;
[M+H]+: m/z 344; [M−H]−: m/z 342

Stage 2:

Separation of the mixture of isomers with respect to the position of the methyl, by chiral chromatography on Chiralpak AD 20 μm (1000 g, diameter 80 mm)
Injection: 60 ml EtOH+40 ml heptane
Mobile phase: 60% EtOH 40% heptane 0.1% TEA
Mobile phase flow rate: 150 ml/mn
UV detection: 240 nm After separation of the chemoisomers, 63 mg of 2-[(5-fluoro-1-methyl-1H-benzimidazol-2-yl)methyl]-6-(morpholin-4-yl)pyrimidin-4(3H)-one are obtained in the form of beige crystals, the characteristics of which are the following:

$^1$H NMR Spectrum (400 MHz): 3.31 to 3.36 (m, 4H); 3.53 to 3.58 (m, 4H); 3.80 (s, 3H); 4.19 (s, 2H); 5.21 (s, 1H); 7.09 (ddd, J=2.5 and 8.8 and 9.8 Hz, 1H); 7.37 (dd, J=2.5 and 9.8 Hz, 1H); 7.54 (dd, J=4.8 and 8.8 Hz, 1H); 11.87 (broad m, 1H)

Mass spectrometry: Method A
Retention time Tr (min)=0.44
[M+H]+: m/z 344; [M−H]−: m/z 342

Example 12

Synthesis of 2-[(7-fluoro-1,3-benzoxazol-2-yl)methyl]-6-(morpholin-4-yl)pyrimidin-4(3H)-one Stage 1:

The product is prepared according to the procedure described in Example 2, stage 2, using 500 mg of sodium [4-(morpholin-4-yl)-6-oxo-1,6-dihydropyrimidin-2-yl]acetate (Example 1, stage 2), 357 mg of 2-amino-6-fluorophenol and 600 mg of N-[3-(dimethylamino)propyl]-N'-ethylcarbodiimide hydrochloride in a mixture of 4 ml of pyridine and 4 ml of dimethylformamide. 335 mg of N-(3-fluoro-2-hydroxyphenyl)-2-[4-(morpholin-4-yl)-6-oxo-1,6-dihydropyrimidin-2-yl]acetamide are obtained in the form of a beige solid, the characteristics of which are the following:

$^1$H NMR Spectrum (400 MHz, d in ppm, $d_6$-DMSO): 3.44 (m, 4H); 3.62 (m, 4H); 3.71 (s, 2H); 5.21 (s, 1H); 6.78 (dt, J=6.0 and 8.1 Hz, 1H); 6.94 (broad t, J=8.1 Hz, 1H); 7.64 (broad d, J=8.1 Hz, 1H); 9.55 to 10.10 (broad m, 2H); 11.69 (broad m, 1H)

Mass spectrometry: Method B
Retention time Tr (min)=2.66
[M+H]+: m/z 349; [M−H]−: m/z 347
Melting point (Köfler bench): above 260° C.

Stage 2:

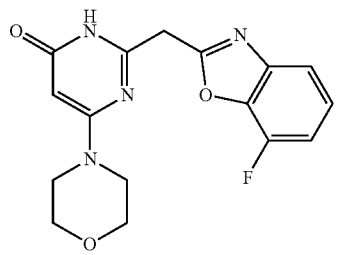 [SMILES: O=c1cc(N2CCOCC2)nc(Cc2nc3cccc(F)c3o2)[nH]1]

42 mg of 4-methylbenzenesulphonic acid hydrate are added to a solution of 300 mg of N-(3-fluoro-2-hydroxyphenyl)-2-[4-(morpholin-4-yl)-6-oxo-1,6-dihydropyrimidin-2-yl]acetamide in 20 ml of xylene. After refluxing for six hours (assembly with Dean-Stark apparatus), the medium is concentrated to dryness under reduced pressure. After purification by silica column chromatography of the solid residue, eluent: gradient of pure $CH_2Cl_2$ to $CH_2Cl_2$/MeOH: 95/05, the product obtained is taken up with twice 20 ml of diethyl ether and then spin-filter-dried and dried under vacuum. 110 mg of 2-[(7-fluoro-1,3-benzoxazol-2-yl)methyl]-6-(morpholin-4-yl)pyrimidin-4(3H)-one are obtained in the form of a white powder, the characteristics of which are the following:

$^1$H NMR Spectrum (400 MHz, d in ppm, $d_6$-DMSO): 3.34 to 3.38 (m, 4H); 3.53 to 3.59 (m, 4H); 4.31 (s, 2H); 5.26 (s, 1H); 7.30 to 7.42 (m, 2H); 7.59 (dd, J=1.4 and 7.7 Hz, 1H); 11.93 (broad m, 1H)

Mass spectrometry: Method B
Retention time Tr (min)=3.11
[M+H]+: m/z 331; [M−H]−: m/z 329

Example 13

Synthesis of 6-(morpholin-4-yl)-2-[(1-phenyl-1H-benzimidazol-2-yl)methyl]pyrimidin-4(3H)-one

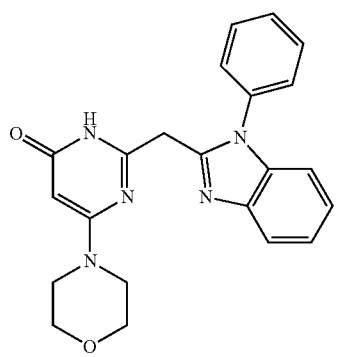 [SMILES: O=c1cc(N2CCOCC2)nc(Cc2nc3ccccc3n2-c2ccccc2)[nH]1]

The product is prepared according to the procedure described in Example 3, using 300 mg of sodium [4-(morpholin-4-yl)-6-oxo-1,6-dihydropyrimidin-2-yl]acetate, 423 mg of N-phenylbenzene-1,2-diamine and 330 mg of N-[3-(dimethylamino)propyl]-N'-ethylcarbodiimide hydrochloride in a mixture of 2.5 ml of pyridine and 2.5 ml of dimethylformamide and then in 5 ml of acetic acid. After purification by silica column chromatography, eluent: $CH_2Cl_2$/MeOH: 95/05, 230 mg of 6-(morpholin-4-yl)-2-[(1-phenyl-1H-benzimidazol-2-yl)methyl]pyrimidin-4(3H)-one are obtained in the form of a white powder, the characteristics of which are the following:

$^1$H NMR Spectrum (400 MHz, d in ppm, $d_6$-DMSO): 3.32 (m, partially broad, 4H); 3.56 (m, 4H); 4.05 (s, 2H); 5.16 (s, 1H); 7.11 to 7.17 (m, 1H); 7.19 to 7.30 (m, 2H); 7.49 to 7.72 (m, 6H); 11.74 (broad m, 1H)

Mass spectrometry: Method A
Retention time Tr (min)=0.66
[M+H]+: m/z 388; [M−H]−: m/z 386

Example 14

Synthesis of 2-[(1-benzyl-1H-benzimidazol-2-yl)methyl]-6-(morpholin-4-yl)pyrimidin-4(3H)-one

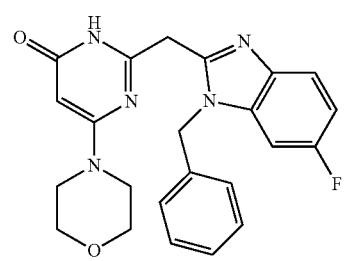 [SMILES: O=c1cc(N2CCOCC2)nc(Cc2nc3ccc(F)cc3n2Cc2ccccc2)[nH]1]

The product is prepared according to the procedure described in Example 3, using 300 mg of sodium [4-(morpholin-4-yl)-6-oxo-1,6-dihydropyrimidin-2-yl]acetate, 455 mg of N-benzylbenzene-1,2-diamine and 330 mg of N-[3-(dimethylamino)propyl]-N'-ethylcarbodiimide hydrochloride in a mixture of 2.5 ml of pyridine and 2.5 ml of dimethylformamide and then in 5 ml of acetic acid. After refluxing for forty-five minutes and purification by silica column chromatography, eluent: $CH_2Cl_2$/MeOH: 95/05, 250 mg of 2-[(1-benzyl-1H-benzimidazol-2-yl)methyl]-6-(morpholin-4-yl)pyrimidin-4(3H)-one are obtained in the form of a cream powder, the characteristics of which are the following:

$^1$H NMR Spectrum (400 MHz, d in ppm, $d_6$-DMSO): 3.25 to 3.35 (m partially masked, 4H); 3.52 to 3.58 (m, 4H); 4.18 (s, 2H); 5.18 (s, 1H); 5.56 (s, 2H); 7.13 to 7.20 (m, 4H); 7.23 to 7.35 (m, 3H); 7.39 to 7.47 (m, 1H); 7.55 to 7.64 (m, 1H); 11.88 (broad m, 1)

Mass spectrometry: Method A
Retention time Tr (min)=0.58
[M+H]+: m/z 402; [M−H]−: m/z 400

Example 15

Synthesis of 2-[(1-ethyl-1H-benzimidazol-2-yl)methyl]-6-(morpholin-4-yl)pyrimidin-4(3H)-one

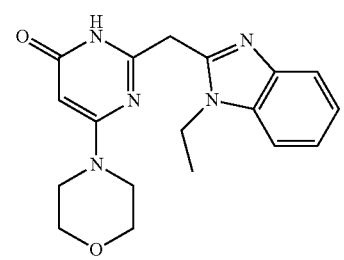 [SMILES: CCn1c(Cc2nc(N3CCOCC3)cc(=O)[nH]2)nc2ccccc21]

Stage 1:

The product is prepared according to the procedure described in Example 3, using 300 mg of sodium [4-(morpholin-4-yl)-6-oxo-1,6-dihydropyrimidin-2-yl]acetate, 248 mg of benzene-1,2-diamine and 330 mg of N-[3-(dimethylamino)propyl]-N'-ethylcarbodiimide hydrochloride in a mixture of 2.5 ml of pyridine and 2.5 ml of dimethylformamide and then in 5 ml of acetic acid. After refluxing for one hour and purification by silica column chromatography, eluent: $CH_2Cl_2$/MeOH: gradient from 100/0 to 90/10, 75 mg of 2-(1H-benzimidazol-2-ylmethyl)-6-(morpholin-4-yl)pyrimidin-4(3H)-one are obtained in the form of a beige powder, the characteristics of which are the following:

Mass spectrometry: Method A
Retention time Tr (min)=0.35
[M+H]+: m/z 312; [M−H]−: m/z 310

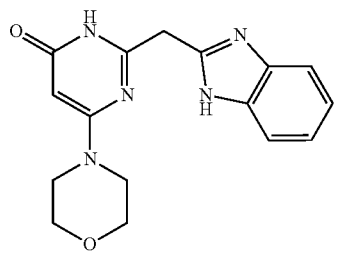 [SMILES: O=c1cc(N2CCOCC2)nc(Cc2nc3ccccc3[nH]2)[nH]1]

Stage 2:

The product can be prepared as in stage 1 of Example 11, but using 155 mg of 2-(1H-benzimidazol-2-ylmethyl)-6-(morpholin-4-yl)pyrimidin-4(3H)-one in 15 ml of acetone, 0.375 ml of sodium hydroxide (2N) and 0.6 ml of iodoethane. After purification by silica column chromatography, eluent: $CH_2Cl_2$/MeOH: 95/05, 30 mg of 2-[(1-ethyl-1H-benzimidazol-2-yl)methyl]-6-(morpholin-4-yl)pyrimidin-4(3H)-one are obtained in the form of a beige powder, the characteristics of which are the following:

$^1$H NMR Spectrum (400 MHz, d in ppm, $d_6$-DMSO): 1.31 (t, J=7.1 Hz, 3H); 3.34 (m, 4H); 3.57 (m, 4H); 4.18 (s, 2H); 4.31 (q, J=7.1 Hz, 2H); 5.21 (s, 1H); 7.13 to 7.19 (m, 1H); 7.20 to 7.25 (m, 1H); 7.51 to 7.59 (m, 2H); 11.88 (broad m, 1H)

Mass spectrometry: Method A
Retention time Tr (min)=0.42
[M+H]+: m/z 340; [M−H]−: m/z 338

Example 16

Synthesis of 2-[(5,6-difluoro-1,3-benzoxazol-2-yl)methyl]-6-(morpholin-4-yl)pyrimidin-4(3H)-one

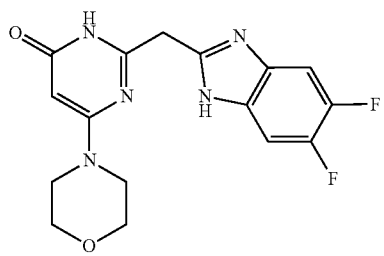 [SMILES: O=c1cc(N2CCOCC2)nc(Cc2nc3cc(F)c(F)cc3[nH]2)[nH]1]

Stage 1:

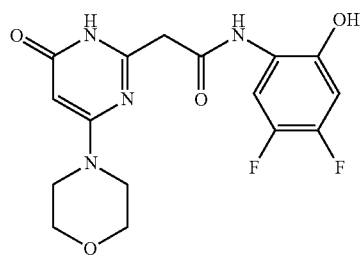 [SMILES: O=C(Cc1nc(N2CCOCC2)cc(=O)[nH]1)Nc1cc(F)c(F)cc1O]

The product is prepared according to the procedure described in stage 1 of Example 2, but using 500 mg of sodium [4-(morpholin-4-yl)-6-oxo-1,6-dihydropyrimidin-2-yl]acetate (Example 1, stage 2), 425 mg of 2-amino-4,5-difluorophenol and 600 mg of N-[3-(dimethylamino)propyl]-N'-ethylcarbodiimide hydrochloride in a mixture of 4 ml of pyridine and 4 ml of dimethylformamide. 500 g of N-(4,5-difluoro-2-hydroxyphenyl)-2-[4-(morpholin-4-yl)-6-oxo-1,6-dihydropyrimidin-2-yl]acetamide are obtained in the form of a brown solid, the characteristics of which are the following:

Mass spectrometry: Method A
Retention time Tr (min)=0.68
[M+H]+: m/z 367; [M−H]−: m/z 365

Stage 2:

The product can be prepared as described in stage 2 of Example 12, but using 465 mg of N-(4,5-difluoro-2-hydroxyphenyl)-2-[4-(morpholin-4-yl)-6-oxo-1,6-dihydropyrimidin-2-yl]acetamide in 30 ml of xylene and 77 mg of 4-methylbenzenesulphonique acid hydrate. After refluxing for six hours, addition of 100 mg of 4-methylbenzenesulphonic acid hydrate and purification by silica column chromatography, eluent: gradient of pure $CH_2Cl_2$ to $CH_2Cl_2$/MeOH: 96/04, the product obtained is taken up with 20 ml of diethyl ether and then spin-filter-dried and dried under vacuum. 63 mg of 2-[(5,6-difluoro-1,3-benzoxazol-2-yl)methyl]-6-(morpholin-4-yl)pyrimidin-4(3H)-one are obtained in the form of a white solid, the characteristics of which are the following:

$^1$H NMR Spectrum (400 MHz, d in ppm, $d_6$-DMSO): 3.35 (m, 4H); 3.56 (m, 4H); 4.26 (s, 2H); 5.24 (broad m, 1H); 7.91 (dd, J=7.6 and 10.3Hz, 1H); 8.04 (dd, J=7.0 and 9.9 Hz, 1H); 11.88 (broad m, 1H)

Mass spectrometry: Method A
Retention time Tr (min)=0.68
[M+H]+: m/z 349; [M−H]−: m/z 347

Example 17

Synthesis of 2-[(6-chloro-1H-benzimidazol-2-yl)methyl]-6-(morpholin-4-yl)pyrimidin-4(3H)-one

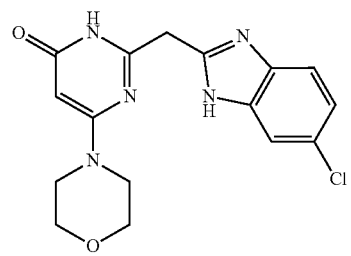 [SMILES: O=c1cc(N2CCOCC2)nc(Cc2nc3ccc(Cl)cc3[nH]2)[nH]1]

The product is prepared according to the procedure described in Example 3, using 400 mg of sodium [4-(morpholin-4-yl)-6-oxo-1,6-dihydropyrimidin-2-yl]acetate, 436 mg of 4-chlorobenzene-1,2-diamine and 440 mg N-[3-(dimethylamino)propyl]-N'-ethylcarbodiimide hydrochloride in a mixture of 3.5 ml of pyridine and 3.5 ml of dimethylformamide and then in 7 ml of acetic acid. After refluxing for thirty minutes and purification by silica column chromatography, eluent: CH$_2$Cl$_2$/MeOH: gradient from 100/0 to 90/10, 260 mg of 2-[(6-chloro-1H-benzimidazol-2-yl)methyl]-6-(morpholin-4-yl)pyrimidin-4(3H)-one are obtained in the form of a white powder, the characteristics of which are the following:

$^1$H NMR Spectrum (400 MHz, d in ppm, d$_6$-DMSO): 3.37 (m, 4H); 3.57 (m, 4H); 4.10 (s, 2H); 5.22 (s, 1H); 7.17 (dd, J=1.9 and 8.6 Hz, 1H); 7.51 (d, J=8.6 Hz, 1H); 7.57 (d, J=1.9 Hz, 1H); 12.18 (broad m, 2H)

Mass spectrometry: Method A

Retention time Tr (min)=0.51

[M+H]+: m/z 346; [M−H]−: m/z 344

Example 18

Synthesis of 2-[(1-cyclopropyl-5-fluoro-1H-benzimidazol-2-yl)methyl]-6-(morpholin-4-yl)pyrimidin-4(3H)-one

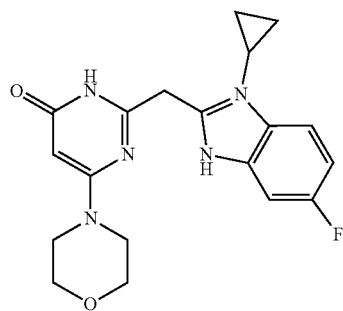

Stage 1:

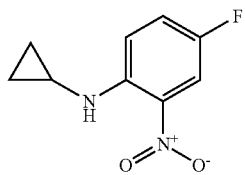 [SMILES: O=[N+]([O-])c1cc(F)ccc1NC1CC1]

In a reactor for a microwave oven, 795 mg of 1,4-difluoro-2-nitrobenzene are introduced into 10 ml of tetrahydrofuran. 1 ml of N-ethyl-N-(propan-2-yl)propan-2-amine and 0.416 ml of cyclopropanamine are added. After thirty minutes at a temperature of 110° C. under microwave irradiation, and then one hour twenty minutes at a temperature of 120° C., 0.1 ml of cyclopropanamine is added and the medium is then again placed at a temperature of 130° C. for thirty minutes under microwave irradiation. After concentration to dryness under reduced pressure, 960 mg of N-cyclopropyl-4-fluoro-2-nitroaniline are obtained in the form of an orange powder which will be used as in the next stage.

Stage 2:

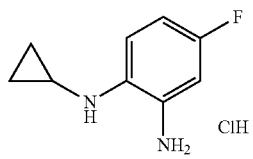 [SMILES: Nc1cc(F)ccc1NC1CC1 ; Cl]

1.58 g of zinc are slowly added to a solution of 950 mg of N-cyclopropyl-4-fluoro-2-nitroaniline in 15 ml of acetic acid. After stirring for one hour thirty minutes at a temperature in the region of 20° C., 25 ml of water are added to the medium and the pH is adjusted to 7 using a 28% aqueous ammonia solution. The aqueous phase is extracted with three times 30 ml of ethyl acetate, and the combined organic phases are dried over anhydrous magnesium sulphate, filtered and concentrated to dryness under reduced pressure. The oily residue is taken up in 100 ml of diethyl ether and an aqueous solution of hydrochloric acid (2N) is added until a precipitate forms. The solid is spin-filter-dried and then dried under a vacuum bell jar, and 960 mg of N$^1$-cyclopropyl-4-fluorobenzene-1,2-diamine hydrochloride are obtained in the form of a purple powder, the characteristics of which are the following:

Mass spectrometry: Method A

Retention time Tr (min)=0.62

[M+H]+: m/z 167

Stage 3:

The product is prepared according to the procedure described in Example 3, using 300 mg of sodium [4-(morpholin-4-yl)-6-oxo-1,6-dihydropyrimidin-2-yl]acetate, 645 mg of N$^1$-cyclopropyl-4-fluorobenzene-1,2-diamine hydrochloride and 330 mg of N-[3-(dimethylamino)propyl]-N'-ethylcarbodiimide hydrochloride in a mixture of 3 ml of pyridine and 3 ml of dimethylformamide and then in 5 ml of acetic acid. After refluxing for two hours and purification by silica column chromatography, eluent: CH$_2$Cl$_2$/MeOH: 95/05, the residue obtained is purified by preparative HPLC/MS (method 1). After the acetonitrile has been evaporated off, the pH is brought to 8 using sodium bicarbonate (solid), then the aqueous phase is extracted with twice 25 ml of ethyl acetate, and the combined organic phases are dried over anhydrous magnesium sulphate, filtered and concentrated to dryness under reduced pressure. 15 mg of 2-[(1-cyclopropyl-5-fluoro-1H-benzimidazol-2-yl)methyl]-6-(morpholin-4-yl)pyrimidin-4(3H)-one are obtained in the form of a white powder, the characteristics of which are the following:

$^1$H NMR Spectrum (400 MHz, d in ppm, d$_6$-DMSO): 1.04 to 1.22 (m, 4H); 3.33 to 3.43 (m, 5H); 3.54 to 3.60 (m, 4H); 4.24 (s, 2H); 5.22 (s, 1H); 7.09 (dt, J=2.4 and 9.3Hz, 1H); 7.39 (dd, J=2.4 and 9.8 Hz, 1H); 7.56 (dd, J=4.8 and 9.3Hz, 1H); 11.80 (broad m, 1H)

Mass spectrometry: Method A

Retention time Tr (min)=0.57

[M+H]+: m/z 370; [M−H]−: m/z 368

Example 19

Synthesis of 2-{[5-fluoro-1-(2-methoxyethyl)-1H-benzimidazol-2-yl]methyl}-6-(morpholin-4-yl)pyrimidin-4(3H)-one

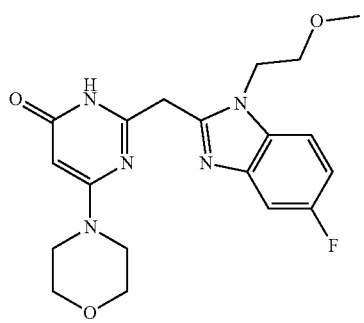 [SMILES: COCCn1c(Cc2nc(N3CCOCC3)cc(=O)[nH]2)nc2cc(F)ccc21]

Stage 1:

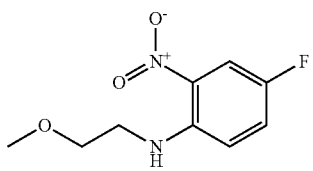

The product can be prepared as described in stage 1 of Example 18, but using 795 mg of 1,4-difluoro-2-nitrobenzene in 10 ml of tetrahydrofuran, 1 ml of N-ethyl-N-(propan-2-yl)propan-2-amine and 0.655 ml of 2-methoxyethanamine. After one hour at a temperature of 130° C. under microwave irradiation, 900 mg of 4-fluoro-N-(2-methoxyethyl)-2-nitroaniline are obtained in the form of a red oil which will be used as in the next stage.

Stage 2:

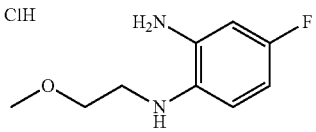

The product can be prepared as described in stage 2 of Example 18, but using 880 mg of 4-fluoro-N-(2-methoxyethyl)-2-nitroaniline in 11 ml of acetic acid, and 1.34 g of zinc. After stirring for three hours at a temperature in the region of 20° C., 536 mg of zinc are added. 850 mg of 4-fluoro-$N^1$-(2-methoxyethyl)benzene-1,2-diamine hydrochloride are obtained in the form of a red oil which will be used as in the next stage.

Stage 3:

The product is prepared according to the procedure described in Example 3, using 300 mg of sodium [4-(morpholin-4-yl)-6-oxo-1,6-dihydropyrimidin-2-yl]acetate, 760 mg of 4-fluoro-$N^1$-(2-methoxyethyl)benzene-1,2-diamine hydrochloride and 330 mg of N-[3-(dimethylamino)propyl]-N'-ethylcarbodiimide hydrochloride in a mixture of 5 ml of pyridine and 5 ml of dimethylformamide and then in 5 ml of acetic acid. After refluxing for one hour and purification by silica column chromatography, eluent: $CH_2Cl_2$/MeOH: 95/05, the residue obtained is purified by preparative HPLC/MS (method 1). After the acetonitrile has been evaporated off, the pH is brought to 8 using sodium bicarbonate (solid), then the aqueous phase is extracted with twice 25 ml of ethyl acetate, and the combined organic phases are dried over anhydrous magnesium sulphate, filtered and concentrated to dryness under reduced pressure. 120 mg of 2-{[5-fluoro-1-(2-methoxyethyl)-1H-benzimidazol-2-yl]methyl}-6-(morpholin-4-yl)pyrimidin-4(3H)-one are obtained in the form of a white powder, the characteristics of which are the following:

$^1$H NMR Spectrum (400 MHz, d in ppm, $d_6$-DMSO): 3.20 (s, 3H); 3.33 to 3.40 (m, 4H); 3.54 to 3.59 (m, 4H); 3.63 (t, J=5.3Hz, 2H); 4.19 (s, 2H); 4.47 (t, J=5.3Hz, 2H); 5.21 (s, 1H); 7.08 (dt, J=2.4 and 9.3Hz, 1H); 7.37 (dd, J=2.4 and 9.8 Hz, 1H); 7.57 (dd, J=4.8 and 9.3Hz, 1H); 11.80 (broad m, 1H)

Mass spectrometry: Method A
Retention time Tr (min)=0.51
[M+H]+: m/z 388; [M−H]−: m/z 386

Example 20

Synthesis of 6-(morpholin-4-yl)-2-(naphtho[2,1-d][1,3]oxazol-2-ylmethyl)pyrimidin-4(3H)-one

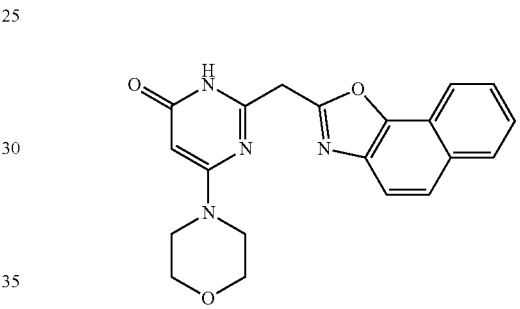

Stage 1:

65 mg of sodium [4-(morpholin-4-yl)-6-oxo-1,6-dihydropyrimidin-2-yl]acetate, 104 mg of 2-(1H-benzotriazol-1-yl)-1,1,3,3-tetramethyluronium hexafluorophosphate (HBTU) and 82 µA of N-methylmorpholine are added to a solution of 40 mg of 3-amino-2-naphthol in 2 ml of dimethylformamide. The reaction mixture is heated for 1 hour at 110° C. and then, after cooling, 0.1 ml of TFA is added and the precipitate is purified by chromatography. The N-(2-naphthol)-2-[4-(morpholin-4-yl)-6-oxo-1,6-dihydropyrimidin-2-yl]acetamide obtained is used as it is in the next stage.

Stage 2:

The N-(2-naphthol)-2-[4-(morpholin-4-yl)-6-oxo-1,6-dihydropyrimidin-2-yl]acetamide obtained in the previous stage is dissolved in 2 ml of trifluoroacetic acid and microwave-irradiated for 30 minutes at 120° C. 8 ml of toluene are added and the solution is concentrated to dryness. After purification by chromatography, 4 mg of 6-(morpholin-4-yl)-2-(naphtho[2,1-d][1,3]oxazol-2-ylmethyl)pyrimidin-4(3H)-one are obtained, the characteristics of which are the following:

$^1$H NMR Spectrum (400 MHz, d in ppm, $d_6$-DMSO): 3.31 to 3.48 (m partially masked, 4H); 3.54 to 3.64 (m, 4H); 4.39 (s, 2H); 5.26 (broad m, 1H); 7.63 (t, J=8.0 Hz, 1H); 7.73 (t, J=8.0 Hz, 1H); 7.87 (d, J=9.0 Hz, 1H); 7.94 (d, J=9.0 Hz, 1H); 8.14 (d, J=8.0 Hz, 1H); 8.21 (d, J=8.0 Hz, 1H); 12.00 (broad m, 1H)

Mass spectrometry: Method A
Retention time Tr (min)=1.02
[M+H]+: m/z 363; [M−H]−: m/z 361

Example 21

Synthesis of 2-[(6-methoxy-1,3-benzoxazol-2-yl)methyl]-6-(morpholin-4-yl)pyrimidin-4(3H)-one

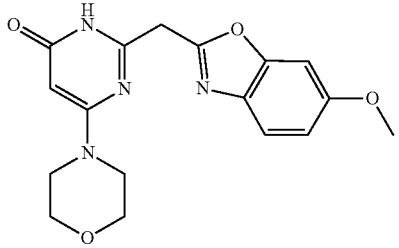 [SMILES: COc1ccc2nc(Cc3nc(N4CCOCC4)cc(=O)[nH]3)oc2c1]

Stage 1:

4 ml of pyridine, 1.2 g of N-[3-(dimethylamino)propyl]-N'-ethylcarbodiimide hydrochloride and 940 mg of 2-hydroxy-4-methoxyaniline are added to a solution of 1 g of sodium [4-(morpholin-4-yl)-6-oxo-1,6-dihydropyrimidin-2-yl]acetate in 6 ml of dimethylformamide. The reaction mixture is stirred at ambient temperature for 2 hours and then concentrated under reduced pressure. Water and ethyl acetate are added and the resulting mixture is thus stirred for 30 minutes. The precipitate formed is filtered off and rinsed with water, ethyl ether and petroleum ether. The solid obtained is dried under vacuum. 1.2 g of N-(4-fluoro-2-hydroxyphenyl)-2-[4-(morpholin-4-yl)-6-oxo-1,6-dihydropyrimidin-2-yl]acetamide are obtained in the form of a brown solid which is used as it is in the next stage.

Mass spectrometry: Method B
Retention time Tr (min)=2.55
[M+H]+: m/z 361; [M−H]−: m/z 359

Stage 2:

500 mg of the N-(4-fluoro-2-hydroxyphenyl)-2-[4-(morpholin-4-yl)-6-oxo-1,6-dihydropyrimidin-2-yl]acetamide are mixed into 40 ml of xylene, and 155 mg of 4-methylbenzenesulphonic acid hydrate are added. The reaction mixture is brought to reflux for 3 hours. After cooling to 20° C., the reaction mixture is concentrated to dryness under reduced pressure and then the residue is chromatographed on a silica gel column, eluent: CH$_2$Cl$_2$/MeOH: 95/05. 220 mg of 2-[(6-methoxy-1,3-benzoxazol-2-yl)methyl]-6-(morpholin-4-yl)pyrimidin-4(3H)-one are thus obtained in the form of a white solid, the characteristics of which are the following:

$^1$H NMR Spectrum (400 MHz): 3.36 (m, 4H); 3.57 (m, 4H); 3.81 (s, 3H); 4.19 (s, 2H); 5.24 (s, 1H); 6.95 (dd, J=2.2 and 8.8 Hz, 1H); 7.33 (d, J=2.2 Hz, 1H); 7.58 (d, J=8.8 Hz, 1H); 11.89 (broad m, 1H)

Mass spectrometry: Method A
Retention time Tr (min)=0.64
[M+H]+: m/z 343; [M−H]−: m/z 341

Example 22

Synthesis of 2-[(6,7-difluoro-1,3-benzoxazol-2-yl)methyl]-6-(morpholin-4-yl)pyrimidin-4(3H)-one

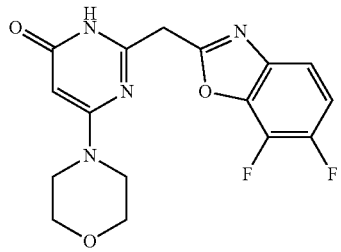

Stage 1:

65 mg of sodium [4-(morpholin-4-yl)-6-oxo-1,6-dihydropyrimidin-2-yl]acetate, 284 mg of 2-(1H-benzotriazol-1-yl)-1,1,3,3-tetramethyluronium hexafluorophosphate (HBTU) and 82 μL of N-methylmorpholine are added to a solution of 32 mg of 6-amino-2,3-difluorophenol in 2 ml of dimethylformamide. The reaction mixture is heated for 1 hour at 110° C. and then, after cooling, 0.1 ml of TFA is added and the precipitate is purified by chromatography. The N-(3,4-fluoro-2-hydroxyphenyl)-2-[4-(morpholin-4-yl)-6-oxo-1,6-dihydropyrimidin-2-yl]acetamide obtained is used as it is in the next stage.

Stage 2:

The N-(3,4-fluoro-2-hydroxyphenyl)-2-[4-(morpholin-4-yl)-6-oxo-1,6-dihydropyrimidin-2-yl]acetamide obtained in the previous stage is dissolved in 2 ml of trifluoroacetic acid and microwave-irradiated for 30 minutes at 120° C. 80 ml of toluene are added and the solution is concentrated to dryness. After purification by chromatography, 4 mg of 2-[(6,7-difluoro-1,3-benzoxazol-2-yl)methyl]-6-(morpholin-4-yl)pyrimidin-4(3H)-one are obtained, the characteristics of which are the following:

$^1$H NMR Spectrum (400 MHz, d in ppm, d$_6$-DMSO): 3.26 to 3.47 (m partially masked, 4H); 3.54 to 3.71 (m, 4H); 4.32 (s, 2H); 5.25 (broad m, 1H); 7.50 (m, 1H); 7.63 (m, 1H); 11.96 (broad m, 1H)

Mass spectrometry: Method A
Retention time Tr (min)=0.97
[M+H]+: m/z 349; [M−H]−: m/z 347

Generic Procedure Used for Examples 23 to 35

Coupling: 1 equivalent of diamine is weighed out and placed in a reactor. 1 ml of a suspension containing 1 equivalent of the sodium salt of (4-morpholin-4-yl-6-oxo-1,6-dihydropyrimidin-2-yl)acetic acid, obtained in stage 2 of Example 1, and 3 equivalents of N-methylmorpholine (109-02-4) in dimethylformamide is then added, followed by 1.1 equivalents of HBTU (94790-37-1) in solution in N,N-dimethylformamide. The reactor is then closed and agitated at 110° C. for one hour. After cooling to ambient temperature, 0.1 ml of trifluoroacetic acid is added to the reaction medium, which is then filtered. The filtrate thus obtained is purified by preparative HPLC.

Cyclization: The purified compound previously obtained is dissolved in 2 ml of glacial acetic acid, and then heated at 100° C. for 3 hours. The solution thus obtained is evaporated; the residue is taken up in 2 ml of a mixture of dimethylformamide and trifluoroacetic acid (19/1) and then filtered; the filtrate is purified by preparative HPLC.

The two-stage protocol described above is applied, on a scale of 0.25 mmol, to the series of diamines that follow (diamine column), resulting in the compounds below (Examples 23 to 35).

The compounds are characterized by LCMS analysis, method C.

| Example | Diamine | Compound obtained | MH+ | Retention time[1] (min.) | Purity (%) |
|---|---|---|---|---|---|
| 23 | 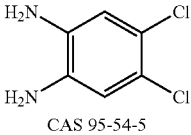 CAS 95-54-5 | 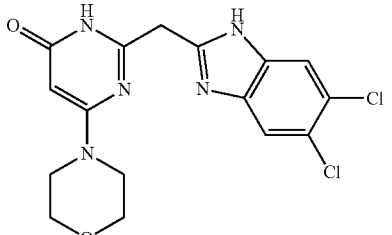 2-[(5,6-dichloro-1H-benzimidazol-2-yl)methyl]-6-(morpholin-4-yl)pyrimidin-4(3H)-one | 380.01 | 0.96 | 98 |
| 24 | 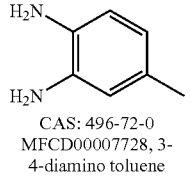 CAS: 496-72-0 MFCD00007728, 3-4-diamino toluene | 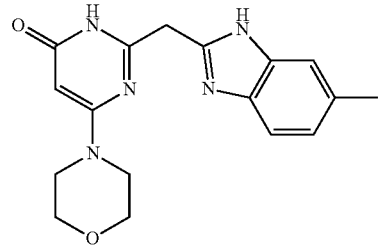 [SMILES: Cc1ccc2nc(Cc3nc(N4CCOCC4)cc(=O)[nH]3)[nH]c2c1] 2-[(6-methyl-1H-benzimidazol-2-yl)methyl]-6-(morpholin-4-yl)pyrimidin-4(3H)-one | 326.13 | 0.74 | 100 |
| 25 | 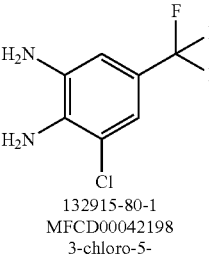 132915-80-1 MFCD00042198 3-chloro-5-trifluoromethyl-1,2-phenylenediamine | 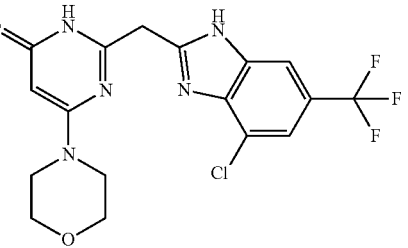 2-{[4-chloro-6-(trifluoromethyl)-1H-benzimidazol-2-yl]methyl}-6-(morpholin-4-yl)pyrimidin-4(3H)-one | 141.04 | 1.02 | 100 |
| 26 | 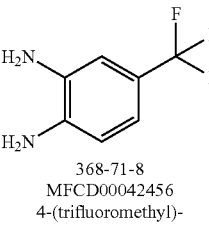 368-71-8 MFCD00042456 4-(trifluoromethyl)-1,2-phenylenediamine | 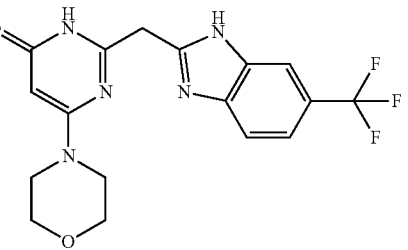 6-(morpholin-4-yl)-2-{[6-(trifluoromethyl)-1H-benzimidazol-2-yl]methyl}pyrimidine-4(3H)-one | 380.05 | 0.93 | 100 |

-continued

| Example | Diamine | Compound obtained | MH+ | Retention time[1] (min.) | Purity (%) |
|---------|---------|-------------------|-----|--------------------------|------------|
| 27 | 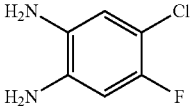 MFCD00042485 4-chloro-5-fluoro-o-phenylenediamine | 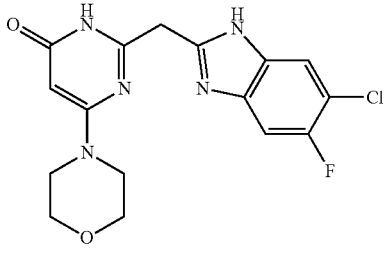 [SMILES: O=c1cc(N2CCOCC2)nc(Cc2nc3cc(F)c(Cl)cc3[nH]2)[nH]1] 2-[(5-chloro-6-fluoro-1H-benzimidazol-2-yl)methyl]-6-(morpholin-4-yl)pyrimidin-4(3H)-one | 364.01 | 0.91 | 100 |
| 28 | 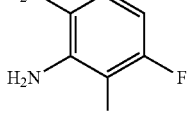 MFCD00153128 1,2-diamino-3,4-difluorobenzene | 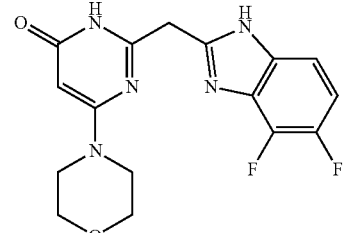 2-[(6,7-difluoro-1H-benzimidazol-2-yl)methyl]-6-(morpholin-4-yl)pyrimidine-4(3H)-one | 348.08 | 0.88 | 100 |
| 29 | 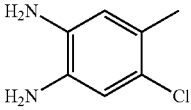 MFCD00221471 63155-04-4 4-chloro-5-methylbenzene-1,2-diamine | 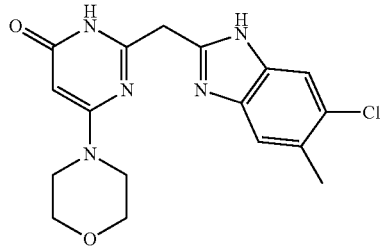 [SMILES: Cc1cc2nc(Cc3nc(N4CCOCC4)cc(=O)[nH]3)[nH]c2cc1Cl] 2-[(5-chloro-6-methyl-1H-benzimidazol-2-yl)methyl]-6-(morpholin-4-yl)pyrimidin-4(3H)-one | 360.06 | 0.88 | 100 |

| Example | Diamine | Compound obtained | MH+ | Retention time[1] (min.) | Purity (%) |
|---|---|---|---|---|---|
| 30 | 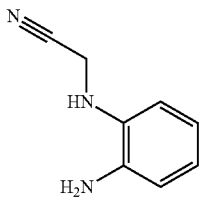 [SMILES: N#CCNc1ccccc1N] MFCD00234427 [(2-aminophenyl)amino]-acetonitrile | 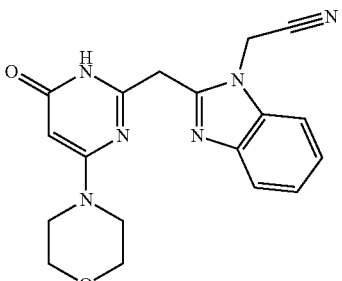 (2-{[4-(morpholin-4-yl)-6-oxo-1,6-dihydropyrimidin-2-yl]methyl}-1H-benzimidazol-1-yl)acetonitrile | 351.1 | 0.85 | 100 |
| 31 | 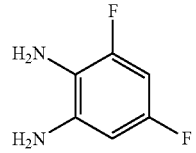 MFCD00973899 1,2-diamino-3,5-difluorobenzene | 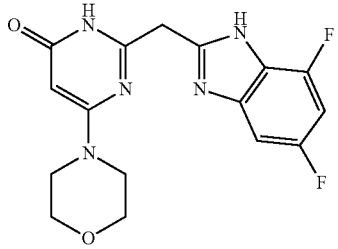 [SMILES: O=c1cc(N2CCOCC2)nc(Cc2nc3cc(F)cc(F)c3[nH]2)[nH]1] 2-[(5,7-difluoro-1H-benzimidazol-2-yl)methyl]-6-(morpholin-4-yl)pyrimidine-4(3H)-one | 348.06 | 0.88 | 100 |
| 32 | 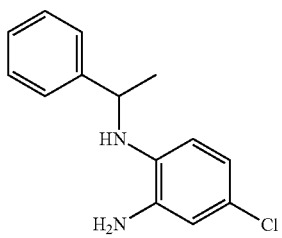 [SMILES: CC(Nc1ccc(Cl)cc1N)c1ccccc1] MFCD02029653 4-chloro-1-n-(1-phenylethyl)benzene-1,2-diamine | 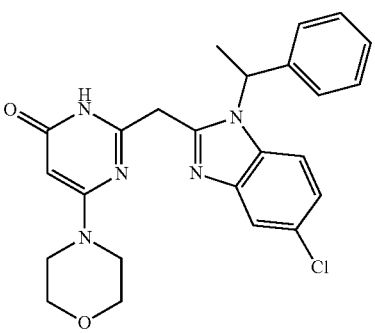 [SMILES: CC(c1ccccc1)n1c(Cc2nc(N3CCOCC3)cc(=O)[nH]2)nc2cc(Cl)ccc21] 2-{[5-chloro-1-(1-phenylethyl)-1H-benzimidazol-2-yl]methyl}-6-(morpholin-4-yl)pyrimidine-4(3H)-one | 450.15 | 1.08 | 98 |

-continued

| Example | Diamine | Compound obtained | MH+ | Retention time[1] (min.) | Purity (%) |
|---|---|---|---|---|---|
| 33 | 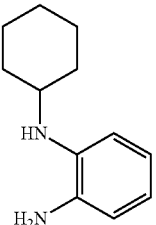 MFCD01120262 n1-cyclohexyl-1,2-benzenediamine | 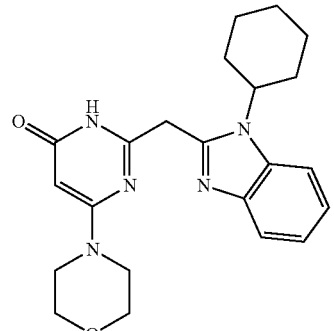 2-[(1-cyclohexyl-1H-benzimidazol-2-yl)methyl]-6-(morpholin-4-yl)pyrimidin-4(3H)-one | 394.19 | 0.92 | 100 |
| 34 | 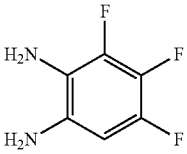 MFCD01569524 1,2-diamino-3,4,5-trifluorobenzene | 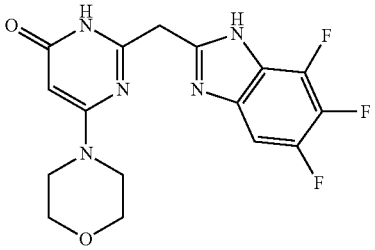 [SMILES: O=c1cc(N2CCOCC2)nc(Cc2nc3cc(F)c(F)c(F)c3[nH]2)[nH]1] 6-(morphlolin-4-yl)-2-[(5,6,7-trifluoro-1H-benzimidazol-2-yl)methyl]pyrimidin-4(3H)-one | 366.03 | 0.93 | 100 |
| 35 | 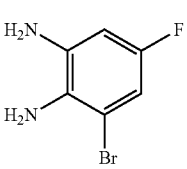 MFCD08741398 3-bromo-1,2-diamino-5-fluorobenzene | 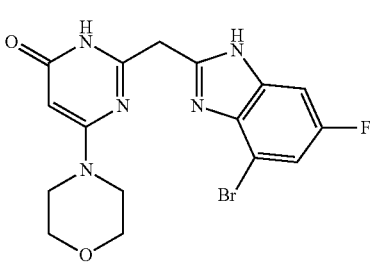 [SMILES: O=c1cc(N2CCOCC2)nc(Cc2nc3c(Br)cc(F)cc3[nH]2)[nH]1] 2-[(4-bromo-6-fluoro-1H-benzimidazol-2-yl)methyl]-6-(morpholin-4-yl)pyrimidin-4(3H)-one | 407.97 | 0.93 | 100 |

Example 36

2-[(6-Bromo-1-methyl-1H-benzimidazol-2-yl)methyl]-6-(morpholin-4-yl)pyrimidin-4(3H)-one

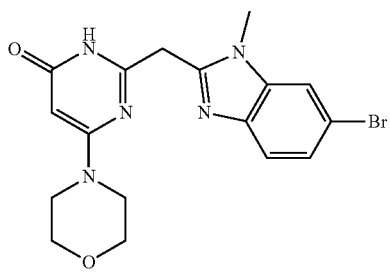 [SMILES: Cn1c(Cc2nc(N3CCOCC3)cc(=O)[nH]2)nc2ccc(Br)cc21]

Stage 1:

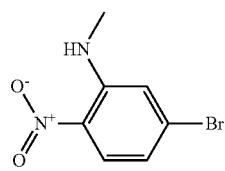

A solution of 4-bromo-2-fluoronitrobenzene (1.2 g) in THF (10 ml) is heated in the presence of N,N-diisopropylethylamine (690 µl) and of methylamine (2M in THF, 3 ml) in a microwave reactor (10° C., 20 min). After 20 min, 100 µl of methylamine THF (2M) are added and the resulting mixture is heated at 105° C. for a further 5 minutes. The reaction medium is concentrated and then taken up in ethyl acetate, and washed with water and then with brine. The organic extracts are combined, dried over magnesium sulphate, filtered and evaporated under reduced pressure. (5-Bromo-2-nitrophenyl)methylamine (1.2 g) is isolated in the form of an orange solid which is used as it is in the next stage.

Stage 2:

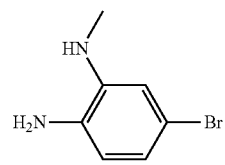

A solution of (5-bromo-2-nitrophenyl)methylamine prepared as above (1.2 g) in acetic acid (20 ml) is treated portionwise with zinc powder (1.72 mg). The reaction medium is stirred at ambient temperature (20° C.) for 90 min. Water and 28% ammonia are added to pH 7, and then the reaction medium is depleted using ethyl acetate. The organic extracts are combined, washed with water and with brine, dried over magnesium sulphate, filtered and evaporated under reduced pressure. The oil obtained is taken up in ether and then 1N HCl is added. The solid formed after evaporation is isolated and dried. 4-Bromo-N2-methylbenzene-1,2-diamine hydrochloride (1.2 g) is obtained and is used as it is in the next stage.

Stage 3:

In a round-bottom flask, the 4-bromo-N2-methylbenzene-1,2-diamine hydrochloride prepared above (1.2 g) is placed in a mixture of DMF (10 ml) and pyridine (10 ml) with magnetic stirring, and then N-(3-dimethylaminopropyl)-N'-ethylcarbodiimide hydrochloride (968 mg) and then the sodium salt of (4-morpholin-4-yl-6-oxo-1,6-dihydropyrimidin-2-yl)acetic acid, obtained in stage 2 of Example 1 (1.2 g) are added. The mixture thus obtained is stirred at ambient temperature (20° C.) overnight. After evaporation of the reaction medium, glacial acetic acid (20 ml) is added and the resulting mixture is brought to reflux (90 min). The reaction medium is concentrated, and taken up in dichloromethane and water at pH 8 (2N sodium hydroxide), so as to form a solid which is filtered off and washed with dichloromethane. The solid obtained is dissolved in methanol, adsorbed onto silica (7 g) and purified by chromatography. Purification is carried out on a silica column (50 g), elution being carried out with a mixture of dichloromethane and 9/1 dichloromethane/MeOH (with CV=75 ml; gradient: 4 CV DCM; 4 CV of 0 to 16% 9/1 DCM/MeOH; 8 CV of 16 to 20% 9/1 DCM/MeOH; 1 CV of 20 to 30% 9/1 DCM/MeOH). The fractions containing the expected compound are combined and evaporated under reduced pressure. 900 mg of 2-[(6-bromo-1-methyl-1H-benzimidazol-2-yl)methyl]-6-(morpholin-4-yl)pyrimidin-4(3H)-one are isolated, the characteristics of which are the following:

$^1$H NMR Spectrum (400 MHz): 3.33 (m, 4H); 3.57 (m, 4H); 3.80 (s, 3H); 4.20 (s, 2H); 5.21 (s, 1H); 7.31 (dd, J=1.7 and 8.6 Hz, 1H); 7.52 (d, J=8.6 Hz, 1H); 7.83 (d, J=1.7 Hz, 1H); 11.81 (broad m, 1H)

Mass spectrometry: Method B
Retention time Tr (min)=2.91;
[M+H]+: m/z 404; [M−H]−: m/z 402

Example 37

2-[(6,7-Difluoro-1-methyl-1H-benzimidazol-2-yl)methyl]-6-(morpholin-4-yl)pyrimidin-4(3H)-one

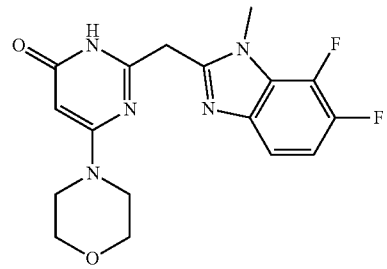 [SMILES: Cn1c(Cc2nc(N3CCOCC3)cc(=O)[nH]2)nc2ccc(F)c(F)c21]

Stage 1:

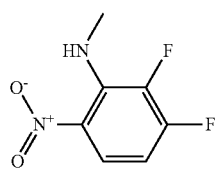

A solution of 2,3-difluoro-6-nitroaniline (3 g) in toluene (9.2 ml) is treated with dimethyl sulphate (2.6 g) and 2N sodium hydroxide (17.3 ml) in the presence of tetrabutylammonium bromide (0.33 g) with stirring at ambient temperature (20° C.) for 24 hours. The reaction medium is run into 2N HCl (150 ml) and the resulting mixture is depleted using dichloromethane (300 ml). The organic extracts are combined, dried over magnesium sulphate, filtered and evaporated under reduced pressure. The compound obtained is purified by silica gel chromatography (300 g silica), elution being carried out with an 85/15 mixture of heptane/ethyl acetate. The fractions containing the expected compound are combined and evaporated under reduced pressure. The desired (2,3-difluoro-6-nitrophenyl)methylamine is isolated and used in the next stage (1.7 g).

Stage 2:

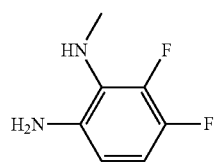

A solution of (2,3-difluoro-6-nitrophenyl)methylamine (500 mg) in acetic acid is treated portionwise with zinc powder (869 mg). The reaction medium is stirred at ambient temperature (20° C.) until complete reduction. Water (13 ml) and 28% ammonia are added to pH 7, and then the reaction medium is depleted using ethyl acetate (3×50). The organic extracts are combined, dried over magnesium sulphate, filtered and evaporated under reduced pressure. The oil obtained is taken up in ether (50 ml) and then treated with 2N HCl. The solid formed is filtered off. 3,4-Difluoro-N1-methylbenzene-1,2-diamine is isolated in its hydrochloride form (510 mg), and is used in the next stage.

Stage 3:

N-(3-Dimethylaminopropyl)-N'-ethylcarbodiimide hydrochloride (220.3 mg) and then the sodium salt of (4-morpholin-4-yl-6-oxo-1,6-dihydro-pyrimidin-2-yl)acetic acid, obtained in stage 2 of Example 1 (200 mg), are added to a solution of 242.3 mg of the amine prepared above, in a mixture of DMF (1.75 ml) and pyridine (1.75 ml), with magnetic stirring. The mixture thus obtained is stirred at ambient temperature (20° C.) overnight. After evaporation of the reaction medium, 3.5 ml of glacial acetic acid are added and the resulting mixture is brought to reflux until the cyclization compound is obtained. The reaction medium is then diluted with water (20 ml) and then 2N sodium hydroxide is added thereto, to pH 7; the reaction medium is extracted with ethyl acetate (3×20 ml). The organic extracts are combined, dried over magnesium sulphate, filtered and evaporated under reduced pressure. The compound obtained is washed with dichloromethane and then dried. 20.8 mg of 2-[(6,7-difluoro-1-methyl-1H-benzimidazol-2-yl)methyl]-6-(morpholin-4-yl)pyrimidin-4(3H)-one are isolated, the characteristics of which are the following:

$^1$H NMR Spectrum (400 MHz): 3.33 (m, 4H); 3.57 (m, 4H); 3.94 (s, 3H); 4.19 (s, 2H); 5.21 (s, 1H); 7.20 (ddd, J=7.5 and 8.8 and 11.7 Hz, 1H); 7.38 (dd, J=3.3 and 8.8 Hz, 1H); 11.81 (broad m, 1H)

Mass spectrometry: Method A

Retention time Tr (min)=0.65;

[M+H]+: m/z 362; [M−H]−: m/z 360

Example 38

2-[(5,6-Dichloro-1-methyl-1H-benzimidazol-2-yl)methyl]-6-(morpholin-4-yl)pyrimidin-4(3H)-one

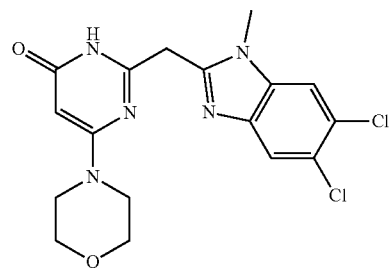 [SMILES: Cn1c(Cc2nc(N3CCOCC3)cc(=O)[nH]2)nc2cc(Cl)c(Cl)cc21]

Stage 1:

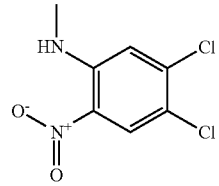

A solution of 4,5-dichloro-2-nitroaniline (3 g) in toluene (9.2 ml) is treated with dimethyl sulphate (2.2 g) and 2N sodium hydroxide (14.5 ml) in the presence of tetrabutylammonium bromide (0.28 g) with stirring at ambient temperature (20° C.) for 24 hours. The reaction medium is run into 2N HCl (150 ml) and the resulting mixture is depleted using dichloromethane (3×100 ml). The organic extracts are combined, dried over magnesium sulphate, filtered and evaporated under reduced pressure. The compound obtained is purified by silica gel chromatography (300 g silica), elution being carried out with an 85/15 mixture of heptane/ethyl acetate. The fractions containing the expected compound are combined and evaporated under reduced pressure. The desired (4,5-dichloro-2-nitrophenyl)methylamine is isolated and is used in the next stage (0.57 g).

Stage 2:

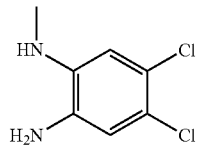

A solution of (4,5-dichloro-2-nitrophenyl)methylamine (500 mg) in acetic acid (7.5 ml) is treated portionwise with zinc powder (740 mg). The reaction medium is stirred at ambient temperature (20° C.) until complete reduction. Water (13 ml) and 28% ammonia are added to pH 7, and then the reaction medium is depleted using ethyl acetate (3×50). The organic extracts are combined, dried over magnesium sulphate, filtered and evaporated under reduced pressure. The oil obtained is taken up in ether (50 ml) and then 2N HCl is added thereto. The solid formed is filtered off. 4,5-Dichloro-N-methylbenzene-1,2-diamine is isolated in its hydrochloride form (510 mg), and is used in the next state.

Stage 3:

N-(3-Dimethylaminopropyl)-N'-ethylcarbodiimide hydrochloride (220.3 mg) and then the sodium salt of (4-morpholin-4-yl-6-oxo-1,6-dihydropyrimidin-2-yl)acetic acid, obtained in stage 2 of Example 1 (200 mg), are added to a solution of 4,5-dichloro-N-methylbenzene-1,2-diamine hydrochloride prepared above (292.7 mg) in a mixture of DMF (1.75 ml) and pyridine (1.75 ml), with magnetic stirring. The mixture thus obtained is stirred at ambient temperature (20° C.) overnight. After evaporation of the reaction medium, 3.5 ml of glacial acetic acid are added and the resulting mixture is brought to reflux until the cyclization compound is obtained. The reaction medium is then diluted with water (20 ml) and then 2N sodium hydroxide is added thereto, to pH 7; the reaction medium is extracted with ethyl acetate (3×20 ml). The organic extracts are combined, dried over magnesium sulphate, filtered and evaporated under reduced pressure. The compound obtained is washed with dichloromethane and then dried. The compound obtained is purified by silica gel chromatography (60 g silica), elution being carried out with an 80/20 mixture of dichloromethane/methanol. The fractions containing the expected compound are combined and evaporated under reduced pressure. 121 mg of 2-[(5,6-dichloro-1-methyl-1H-benzimidazol-2-yl)methyl]-6-(morpholin-4-yl)pyrimidin-4(3H)-one are isolated, the characteristics of which are the following:

$^1$H NMR Spectrum (400 MHz): 3.32 (m, 4H); 3.56 (m, 4H); 3.80 (s, 3H); 4.21 (s, 2H); 5.21 (s, 1H); 7.85 (s, 1H); 7.94 (s, 1H); 11.82 (broad m, 1H)

Mass spectrometry: Method A
Retention time Tr (min)=0.75;
[M+H]+: m/z 394; [M−H]−: m/z 392

Example 39

6-(Morpholin-4-yl)-2-[(5,6,7-trifluoro-1-methyl-1H-benzimidazol-2-yl)methyl]pyrimidin-4(3H)-one

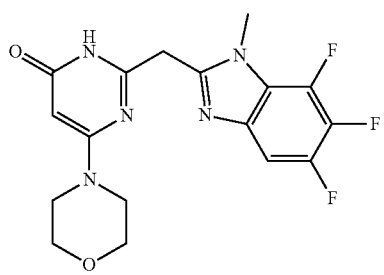 [SMILES: Cn1c(Cc2nc(N3CCOCC3)cc(=O)[nH]2)nc2cc(F)c(F)c(F)c21]

Stage 1:

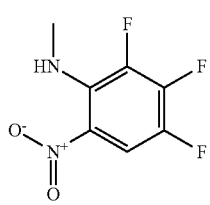

A solution of 2,3,4-trifluoro-6-nitroaniline (3 g) in toluene (8.3 ml) is treated with dimethyl sulphate (2.4 g) and 2N sodium hydroxide (15.6 ml) in the presence of tetrabutylammonium bromide (0.3 g), with stirring at ambient temperature (20° C.) for 48 hours. The reaction medium is run into 2N HCl (150 ml) and then the resulting mixture is depleted using dichloromethane (3×300 ml). The organic extracts are combined, dried over magnesium sulphate, filtered and evaporated under reduced pressure. The compound obtained is purified by silica gel chromatography (300 g silica), elution being carried out with an 85/15 mixture of heptane/ethyl acetate. The fractions containing the expected compound are combined and evaporated under reduced pressure. Methyl(3,4,5-trifluoro-2-nitrophenyl)amine (2 g) is isolated and is used in the next stage.

Stage 2:

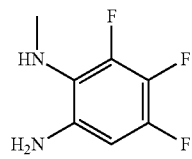

A solution of methyl(3,4,5-trifluoro-2-nitrophenyl)amine (0.5 g) in acetic acid (7.5 ml) is treated portionwise with zinc powder (793 mg). The reaction medium is stirred at ambient temperature (20° C.) until complete reduction. Water (13 ml) and 28% ammonia are added to pH 7, and then the reaction medium is depleted using ethyl acetate (3×50). The organic extracts are combined, dried over magnesium sulphate, filtered and evaporated under reduced pressure. The oil obtained is taken up in ether (50 ml) and then 2N HCl is added thereto. The solid formed is filtered off. 3,4,5-Trifluoro-N$^1$-methylbenzene-1,2-diamine is isolated in its hydrochloride form (508 mg), and is used in the next stage.

Stage 3:

N-(3-Dimethylaminopropyl)-N'-ethylcarbodiimide hydrochloride (220.3 mg) and then the sodium salt of (4-morpholin-4-yl-6-oxo-1,6-dihydro-pyrimidin-2-yl)acetic acid, obtained in stage 2 of Example 1 (200 mg), are added to a solution of 3,4,5-trifluoro-N1-methylbenzene-1,2-diamine prepared above (270 mg) in a mixture of DMF (1.75 ml) and pyridine (1.75 ml), with magnetic stirring. The mixture thus obtained is stirred at ambient temperature (20° C.) overnight. After evaporation of the reaction medium, 3.5 ml of glacial acetic acid are added and the resulting mixture is brought to reflux until the cyclization compound is obtained. The reaction medium is then diluted with water (20 ml) at pH 7; the reaction medium is extracted with ethyl acetate (3×20 ml). The organic extracts are combined, dried over magnesium sulphate, filtered and evaporated under reduced pressure. The compound obtained is washed with dichloromethane and then dried. The compound obtained is purified by silica gel chromatography (100 g silica), elution being carried out with an 80/20 mixture of dichloromethane/methanol. The fractions containing the expected compound are combined and evaporated under reduced pressure. 44 mg of 6-(morpholin-4-yl)-2-[(5,6,7-trifluoro-1-methyl-1H-benzimidazol-2-yl)methyl]pyrimidin-4(3H)-one are isolated, the characteristics of which are the following:

$^1$H NMR Spectrum (400 MHz): 3.33 (m, 4H); 3.57 (m, 4H); 3.94 (s, 3H); 4.20 (s, 2H); 5.21 (broad s, 1H); 7.55 (ddd, J=1.5 and 6.4 and 10.5 Hz, 1H); 11.82 (broad m, 1H)

Mass spectrometry: Method A
Retention time Tr (min)=0.72;
[M+H]+: m/z 380; [M−H]−: m/z 378

Example 40

Synthesis of 2-[(4-hydroxy-1,3-benzoxazol-2-yl)methyl]-6-(morpholin-4-yl)pyrimidin-4(3H)-one

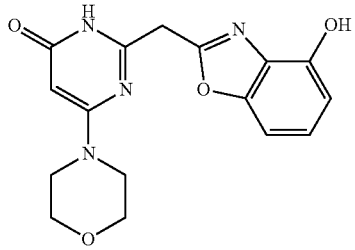 [SMILES: O=c1cc(N2CCOCC2)nc(Cc2nc3c(O)cccc3o2)[nH]1]

Stage 1:

1.19 g of N-[3-(dimethylamino)propyl]-N'-ethylcarbodiimide hydrochloride and 946 mg of 2-aminoresorcinol are added to a solution of 1 g of sodium [4-(morpholin-4-yl)-6-oxo-dihydropyrimidin-2-yl]acetate in 8 ml of pyrimidine. The reaction mixture is stirred at ambient temperature for 18 hours, and then concentrated under reduced pressure. Water and ethyl acetate are added and the resulting mixture is thus stirred for 30 minutes. The precipitate formed is filtered off, and rinsed with water, ethyl ether and petroleum ether. The solid obtained is dried under vacuum. 904 mg of N-(2,6-dihydroxyphenyl)-2-[4-(morpholin-4-yl)-6-oxo-1,6-dihydropyrimidin-2-yl]-acetamide are obtained in the form of a red solid, which is used as it is in the next stage.

Mass spectrometry: Method B
Retention time Tr (min)=2.15
[M+H]+: m/z 347; [M−H]−: m/z 345

Stage 2:

239 mg of 4-methylbenzenesulphonic acid hydrate are added to a solution of 870 mg of N-(2,6-dihydroxyphenyl)-2-[4-(morpholin-4-yl)-6-oxo-1,6-dihydropyrimidin-2-yl]acetamide in 60 ml of ortho-xylene. The reaction mixture is brought to reflux for 4 hours. After cooling to 0° C., the insoluble material formed is filtered off. The filtrate is concentrated to dryness under reduced pressure and then the residue is chromatographed on a silica gel column, elution being carried out with 90/10 $CH_2Cl_2$/MeOH. 654 mg of 2-[(4-hydroxy-1,3-benzoxazol-2-yl)methyl]-6-(morpholin-4-yl)pyrimidin-4(3H)-one are thus obtained in the form of a white solid, the characteristics of which are the following:

$^1$H NMR Spectrum (400 MHz, d in ppm, $d_6$-DMSO): 3.37 (m, 4H); 3.57 (m, 4H); 4.20 (s, 2H); 5.25 (s, 1H); 6.73 (d, J=7.9 Hz, 1H); 7.09 (d, J=7.9 Hz, 1H); 7.16 (t, J=7.9 Hz, 1H); 10.23 (broad s, 1H); 11.92 (broad m, 1H)

Mass spectrometry: Method A
Retention time Tr (min)=0.56
[M+H]+: m/z 329; [M−H]−: m/z 327

Example 41

2-[(7-Bromo-1-methyl-1H-benzimidazol-2-yl)methyl]-6-(morpholin-4-yl)pyrimidin-4(3H)-one

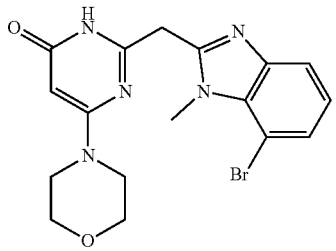 [SMILES: Cn1c(Cc2nc(N3CCOCC3)cc(=O)[nH]2)nc2cccc(Br)c21]

Stage 1:

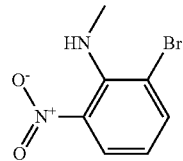

A solution of 3-bromo-2-fluoronitrobenzene (1 g) in THF (8.3 ml) is heated in the presence of N,N-diisopropylethylamine (690 µA) and of methylamine (2.54 ml) in a microwave reactor (105° C., 30 min). The reaction medium is concentrated and then taken up in ethyl acetate, and then washed with water and then with brine. The organic extracts are combined, dried over magnesium sulphate, filtered and evaporated under reduced pressure. (2-Bromo-6-nitrophenyl)methylamine (1 g) is isolated in the form of an orange solid, and is used as it is in the next stage.

Stage 2:

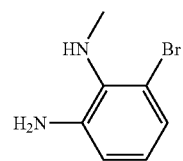

A solution of (2-bromo-6-nitrophenyl)methylamine (1 g) in acetic acid (20 ml) is treated portionwise with zinc powder (1.41 mg). The reaction medium is stirred at ambient temperature (20° C.) until complete reduction. Water and 28% ammonia are added to pH 7 and then the reaction medium is depleted using ethyl acetate (3×50). The organic extracts are combined, washed with water and with brine, dried over magnesium sulphate, filtered and evaporated under reduced pressure. The oil obtained is taken up in ether and then 1N HCl is added thereto. The solid formed after evaporation is isolated and dried. 3-Bromo-N2-methylbenzene-1,2-diamine hydrochloride (1 g) is obtained and is used as it is in the next stage.

Stage 3:

N-(3-Dimethylaminopropyl)-N'-ethylcarbodiimide hydrochloride (807 mg) and then the sodium salt of (4-morpholin-4-yl-6-oxo-1,6-dihydro-pyrimidin-2-yl)acetic acid, obtained in stage 2 of Example 1 (1 g), are added to a solution of 3-bromo-N2-methylbenzene-1,2-diamine hydrochloride prepared above (1 g) in a mixture of DMF (8.3 ml) and pyridine (8.3 ml), with magnetic stirring. The mixture thus obtained is stirred at ambient temperature (20° C.) overnight. After evaporation of the reaction medium, glacial acetic acid (20 ml) is added and the resulting mixture is brought to reflux (90 min). The reaction medium is concentrated, and taken up in dichloromethane and water at pH 8 (2N sodium hydroxide); a solid forms, which is filtered and washed with dichloromethane. The solid obtained is dissolved in methanol, adsorbed onto silica (7 g) and purified by chromatography. Purification is carried out on a silica column (50 g), elution being carried out with a mixture of dichloromethane and 9/1 dichloromethane/MeOH (with CV=75 ml; gradient: 4 CV DCM; 4 CV of 0 to 16% 9/1 DCM/MeOH; 8 CV of 16 to 20% 9/1 DCM/MeOH; 1 CV of 20 to 30% 9/1 DCM/MeOH). The fractions containing the expected compound are combined and evaporated under reduced pressure. 100 mg of 2-[(7-- bromo-1-methyl-1H-benzimidazol-2-yl)methyl]-6-(morpholin-4-yl)pyrimidin-4(3H)-one are isolated, the characteristics of which are the following:

$^1$H NMR Spectrum (400 MHz): 3.34 (m, 4H); 3.57 (m, 4H); 4.05 (s, 3H); 4.21 (s, 2H); 5.21 (s, 1H); 7.09 (t, J=7.8 Hz, 1H); 7.40 (d, J=7.8 Hz, 1H); 7.58 (d, J=7.8 Hz, 1H); 11.82 (broad m, 1H)

Mass spectrometry: Method B
Retention time Tr (min)=3.02;
[M+H]+: m/z 404; [M−H]−: m/z 402

Example 14

Pharmaceutical Composition

Tablets corresponding to the following formulation were prepared:

| | |
|---|---|
| Product from Example 1 | 0.2 g |
| Excipient for a tablet having a final weight of | 1 g |
| (details of the excipient: lactose, talc, starch, magnesium stearate). | |

Example 1 is taken by way of example of a pharmaceutical preparation, it being possible for this preparation to be carried out, if desired, with other products given in examples in the present application.

Pharmacological Section:
Experimental Protocols
In Vitro Experimental Procedures The inhibitory activity of the molecules on AKT phosphorylation is measured either by western blotting using the technique described below, or by the MSD Multi-spot Biomarker detection technique from Meso Scale Discovery also described below. It was demonstrated, on one set of molecules, that both techniques give compatible results.

Study of pAKT expression in PC3 human prostate carcinoma cells measured by western blotting (test A):

This test is based on measuring the expression of the AKT protein phosphorylated on serine 473. The phosphorylation of AKT (pAKT) is measured by western blotting in the PC3 human prostate carcinoma line (ATCC CRL-1435), using an antibody that specifically recognises pAKT-5473.

On day 1, the PC3 cells are seeded into 6-well plates (TPP, #92006) at the concentration of $0.8 \times 10^6$ cells/well in 1800 µl of DMEM medium (DMEM Gibco #11960-044) containing 10% of foetal calf serum (SVF Gibco, #10500-056) and 1% glutamine (L-Glu Gibco #25030-024), and incubated at 37° C., 5% $CO_2$, overnight.

On day 2, the cells are incubated in the presence or absence of the test products for 1 to 2 hours at 37° C. in the presence of 5% $CO_2$. The molecules, diluted in dimethyl sulphoxide (DMSO Sigma #D2650), are added from a 10-times concentrated stock solution, the final percentage of DMSO being 0.1%. The molecules are tested either at a single concentration of less than or equal to 10 µM, or at increasing concentrations in a range that can extend from less than 1 nM to 10 µM.

After this incubation, the cells are lysed for the preparation of the proteins. After the culture medium has been drawn off, the cells are rinsed with 1 ml of PBS (DPBS Gibco, #14190-094), recovered by scraping in 200 µl of complete HNTG buffer and transferred into a 96-well plate (Greiner #651201), and lysed for 1 h on ice. The HNTG buffer is composed of the following mixture: 50 mM hepes, 150 mM NaCl, 1% triton, 10% glycerol, with extemporaneous addition of one Mini Protease Inhibitor Cocktail tablet (Roche 1836153) and of one Phosphatase Inhibitor Cocktail tablet (Roche 104906837001) per 10 ml of buffer.

The lysate is centrifuged for 10 min at 6000 rpm. 155 µl of supernatant are recovered. 150 µl are incubated for denaturation for 5 min at 95° C. in the presence of 4× NuPAGE LDS Sample Buffer diluted 4-fold (InVitrogen ref NP0007) and of 10× NuPAGE Sample Reducing Agent diluted 10-fold (InVitrogen ref NP0009). These samples are then frozen at −20° C. 5 µl are assayed by the microBCA technique according to the technical bulletin of the MicroBCA Protein Assay Kit (Pierce #23235).

For protein separation, 20 µg of proteins are loaded on to a NU-PAGE 4-12% Bis Tris Gel 12 well (InVitrogen ref NP0322BOX) and the migration is carried out for 1 h 30 in 20×NU-PAGE MOPS SDS Running Buffer diluted 20-fold (InVitrogen ref NP0001), at 150 volts.

The gel is then transferred onto an Invitrolon PVDF membrane (Invitrogen #LC2007) permeabilised beforehand for a few seconds in ethanol (Ethanol Fischer Scientific #E/0600DF/15).

The transfer is carried out in a Biorad tank at 30 volts overnight or at 60 volts for 3 hours, in the presence of 20× NUPAGE Transfer Buffer diluted 20-fold (InVitrogen ref NP0006).

The membrane is then saturated in saturating solution composed of TBS (10× Tris Buffered Saline, Sigma #T5912, diluted 10-fold), 0.1% Tween 20 (Sigma #P5927) and 3% BSA (Bovine Serum Albumin Fraction V, Sigma #A4503) for 6 h after overnight transfer or else for 1 h after transfer for a period of 3 h.

The primary antibodies are diluted to 1/1000th for the anti-phospho AKT-Ser473 antibody (193H2, rabbit monoclonal, cat#4058 from Cell Signaling Technology) Abcam), in saturating solution composed of PBS, 0.1% Tween 20 and 3% BSA, and then shaken overnight at 4° C.

Two rinses for 5 min in washing solution composed of TBS and 0.1% Tween 20 are carried out before hybridisation of the secondary antibodies.

The secondary antibodies are diluted 1/10000th for the rabbit anti-Mouse IgG HRP antibody (W402 Promega) and to 1/10000th for the goat anti-Rabbit IgG HRP antibody (W401 Promega) in saturating solution, and then shaken for 1 h at ambient temperature.

Two rinses for 30 min in washing solution are carried out and then a rinse for 5 min in $H_2O$ is carried out in order to eliminate the remaining Tween 20.

The revealing solution is prepared volume-for-volume according to the technical bulletin of the Western Lightning Chemiluminescence Reagent Plus (Western Lightning Chemiluminescence Reagent Plus Perkin Elmer #NEL104).

The membrane is placed in the revealing solution for 1 min, drained, inserted between two transparent plates and then placed in the measuring device for reading the luminescence and the quantification of the signal. The luminescence is read with the FujiFilm device (Ray Test).

The FUJI device measures the total luminescence signal obtained (AU) for each band selected. It then subtracts the background noise (BG) proportional to the size of the band selected (Area), said background noise being calculated from a specific background noise band, with a view to obtaining the specific signal (AU-BG) for each band. The band obtained in the absence of product and in the presence of 0.1% DMSO is considered to be the 100% signal. The software calculates the % specific activity (Ratio) obtained for each band selected as a function of this 100% signal. The percentage inhibition is calculated for each concentration according to the formula (100%−Ratio).

Two independent experiments make it possible to calculate the mean of the percentages of inhibition obtained at a given concentration for the products tested only at one concentration.

Where appropriate, the activity of the products is translated into approximately IC50, obtained from a dose-response curve of various concentrations tested and representing the dose giving 50% of specific inhibition (absolute IC50). Two independent experiments make it possible to calculate the mean of the IC50s. Study of pAKT expression in PC3 human prostate carcinoma cells measured by the MSD Multi-spot Biomarker Detection technique from Meso Scale Discovery (Test B): This test is based on measuring the expression of the AKT protein phosphorylated on serine 473 (P-AKT-S473), in the PC3 human prostate carcinoma line, by means of the technique based on a sandwich immunoassay using the MSD Multi-spot Biomarker Detection kit from Meso Scale Discovery: phospho-Akt (Ser473) whole cell lysate kit (#K151 CAD) or phospho-Akt (Ser473)/Total Akt whole cell lysate kit (#K151OOD).

The primary antibody specific for P-AKT-5473 (Kit #K151 CAD) is coated onto an electrode in each well of the 96-well plates of the MSD kit: after the addition of a protein lysate to each well, the signal is visualised by adding a secondary detection antibody labelled with an electrochemoluminescent compound. The procedure followed is that described in the kit.

On day 1, the PC3 cells are seeded into 96-well plates (TPP, #92096) at the concentration of 35 000 cells/well in 200 µl of DMEM medium (DMEM Gibco #11960-044) containing 10% of foetal calf serum (FCS Gibco, #10500-056) and 1% glutamine (L-Glu Gibco #25030-024), and incubated at 37° C., 5% $CO_2$, overnight.

On day 2, the cells are incubated in the presence or absence of the test products for 1 to 2 h at 37° C. in the presence of 5% of $CO_2$. The molecules, diluted in dimethyl sulphoxide (DMSO Sigma #D2650), are added from a 20-times concentrated stock solution, the final percentage of DMSO being 0.1%. The molecules are tested either at a single concentration of less than or equal to 10 µM, or at increasing concentrations in a range that can extend from less than 1 nM to 10 µM.

After this incubation, the cells are lysed for the preparation of the proteins. For this, after the culture medium has been drawn off, 50 µA of complete Tris Lysis Buffer of the MSD kit containing the protease and phosphatase inhibitor solutions are added to the wells and the cells are lysed for 1 h at 4° C. with shaking At this stage, the plates containing the lysates can be frozen at −20° C. or at −80° C.

The wells of the 96-well plates of the MSD kit are saturated for 1 h at ambient temperature with the blocking solution of the MSD kit. Four washes are carried out with 150 µl of Tris Wash Buffer of the MSD kit. The lysates previously prepared are transferred into the 96-well multi-spot plates of the MSD kit and incubated for 1 h at ambient temperature, with shaking Four washes are carried out with 150 µl of Tris Wash Buffer of the MSD kit. 25 µl of the MSD sulpho-tag detection antibody solution are added to the wells and incubated for 1 h at ambient temperature, with shaking Four washes are carried out with 150 µl of Tris Wash Buffer of the MSD kit. 150 µl of Read Buffer of the MSD kit are added to the wells and the plates are read immediately on the 512400 instrument from Meso Scale Discovery.

The instrument measures a signal for each well. Wells without cells and containing the lysis buffer serve to determine the background noise that will be subtracted from all the measurements (min). The wells containing cells in the absence of product and in the presence of 0.1% DMSO are considered to be the 100% signal (max). The percentage inhibition is calculated for each concentration of test product according to the following formula: (1−((test−min)/(max−min)))×100.

The activity of the product is translated to $IC_{50}$, obtained from a dose-response curve of various concentrations tested and representing the dose giving 50% specific inhibition (absolute $IC_{50}$). Two independent experiments make it possible to calculate the mean of the $IC_{50}$ values.

The results obtained for the products as examples in the experimental section are given in the pharmacological results table below:

Pharmacological Results Table:

| Example | Test A* | Test B* |
|---|---|---|
| Example 1 | 298 | 41 |
| Example 2 | 388 | |
| Example 3 | 1343 | 85 |
| Example 4 | | 475 |
| Example 5 | 1014 | |
| Example 6 | 380 | 49 |
| Example 7 | 903 | 26 |
| Example 8 | | 143 |
| Example 9 | | 175 |
| Example 10 | 713 | 27 |
| Example 11 | | 16 |
| Example 12 | | 88 |
| Example 13 | | 8 |
| Example 14 | | 105 |
| Example 15 | | 26 |
| Example 16 | | 187 |
| Example 17 | | 63 |
| Example 18 | | 9 |
| Example 19 | | 109 |
| Example 20 | | 1000 |
| Example 21 | | 18 |
| Example 22 | | 28 |
| Example 23 | | 193 |
| Example 24 | | 140 |
| Example 25 | | 3000 |
| Example 26 | | 961 |
| Example 27 | | 256 |
| Example 28 | | 585 |
| Example 29 | | 506 |
| Example 30 | | 1340 |
| Example 31 | | 144 |
| Example 32 | | 206 |
| Example 33 | | 142 |
| Example 34 | | 208 |
| Example 35 | | 115 |
| Example 36 | | 28 |
| Example 37 | | 15 |
| Example 38 | | 65 |
| Example 39 | | 100 |
| Example 40 | | 44 |
| Example 41 | | 32 |

*Tests A and B: $IC_{50}$ (nM)

While this invention has been particularly shown and described with references to example embodiments thereof, it will be understood by those skilled in the art that various changes in form and details may be made therein without departing from the scope of the invention encompassed by the appended claims.

We claim:
1. A compound of formula (I):

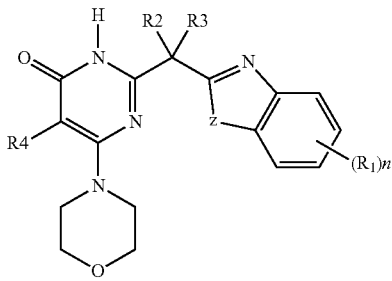

in which:
Z represents —O—, —NH, or Nalk;
n represents an integer from 0 to 4;
R1 represents a halogen atom or a hydroxyl, alkyl or alkoxy radical; the alkyl and alkoxy radicals being optionally substituted with an NRxRy group
R2 and R3, which may be identical or different, represent a hydrogen atom, a halogen atom, or an alkyl radical optionally substituted with one or more halogen atoms;
R4 represents a hydrogen atom;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted with one or more radicals, which may be identical or different, chosen from halogen atoms and alkyl, hydroxyl, oxo, alkoxy, NH2, NHalk and N(alk)$_2$ radicals;
all the above alkyl (alk) and alkoxy radicals being linear or branched and containing from 1 to 6 carbon atoms,
said compound of formula (I) being in all the possible racemic, enantiomeric and diastereoisomeric isomer forms, and also the addition salts with inorganic and organic acids or with inorganic and organic bases, of said compound of formula (I).

2. The compound of claim 1, wherein:
Z represents —O—, —NH or Nalk,
n represents an integer from 0 to 4;
R1 represents a halogen atom or an alkyl or alkoxy radical;
R2 and R3, represent a hydrogen atom;
R4 represents a hydrogen atom;
NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted;
wherein the alkyl (alk) and alkoxy radicals are linear or branched and containing from 1 to 6 carbon atoms, wherein
said compound of formula (I) being in all the possible racemic, enantiomeric and diastereoisomeric isomer forms, and also the addition salts with inorganic and organic acids or with inorganic and organic bases, of said compound of formula (I).

3. The compound of claim 1, which is
2-[(5-fluoro-1H-benzimidazol-2-yl)methyl]-6-(morpholin-4-yl)pyrimidin-4(3H)-one;
2-(1,3-benzoxazol-2-ylmethyl)-6-(morpholin-4-yl)pyrimidin-4(3H)-one
2-[(6-bromo-1H-benzimidazol-2-yl)methyl]-6-(morpholin-4-yl)pyrimidin-4(3H)-one;
2-[(6-methoxy-1H-benzimidazol-2-yl)methyl]-6-(morpholin-4-yl)pyrimidin-4(3H)-one;
2-[(5,6-difluoro-1H-benzimidazol-2-yl)methyl]-6-(morpholin-4-yl)pyrimidin-4(3H)-one;
2-[(6-fluoro-1,3-benzoxazol-2-yl)methyl]-6-(morpholin-4-yl)pyrimidin-4(3H)-one;
2-[(5-fluoro-1,3-benzoxazol-2-yl)methyl]-6-(morpholin-4-yl)pyrimidin-4(3H)-one; or a pharmaceutically acceptable addition salt with an inorganic acid or organic acid or with an inorganic or organic base thereof.

4. A process for preparing a compound of claim 1 of formula (I)-a, said process having the steps of Scheme 1 A:

Scheme 1A:

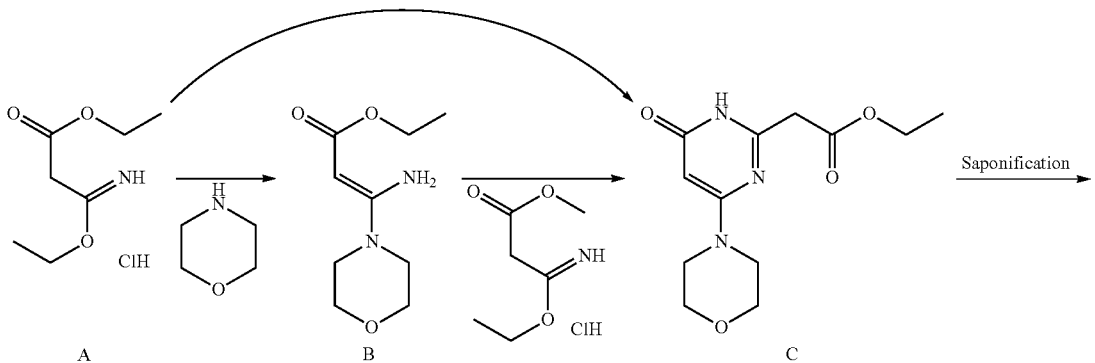

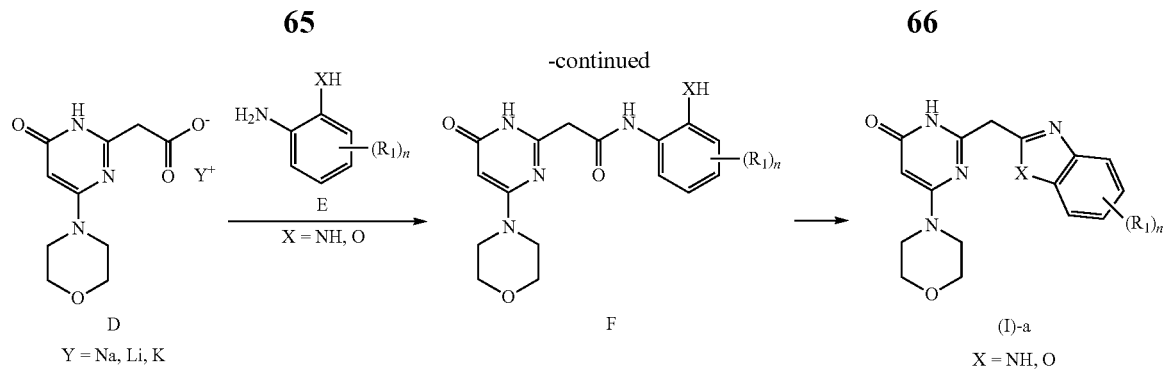

Y = Na, Li, K

X = NH, O in which the substituent R1
represents a halogen atom or a hydroxyl, alkyl or alkoxy radical, the alkyl and alkoxy radicals being optionally substituted with an NRxRy group, NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted.

5. A process for preparing a compound of claim 1, of formula (I)-b, said process having the steps of Scheme 1 B:

in which R1 represents a halogen atom or a hydroxyl, alkyl or alkoxy radical; the alkyl and alkoxy radicals being optionally substituted with an NRxRy group;
R2 and R3, which may be identical or different, represent a hydrogen atom, a halogen atom, or an alkyl radical optionally substituted with one or more halogen atoms; and NRxRy being such that Rx represents a hydrogen atom or an alkyl radical and Ry represents a hydrogen atom or an alkyl radical; or Rx and Ry form, with the nitrogen atom to which they are attached, a cyclic radical containing from 3 to 10 ring members and optionally one or more other heteroatoms chosen from O, S, NH and N-alkyl, this cyclic radical being optionally substituted with one or more radicals, which may be identical Scheme 1B:

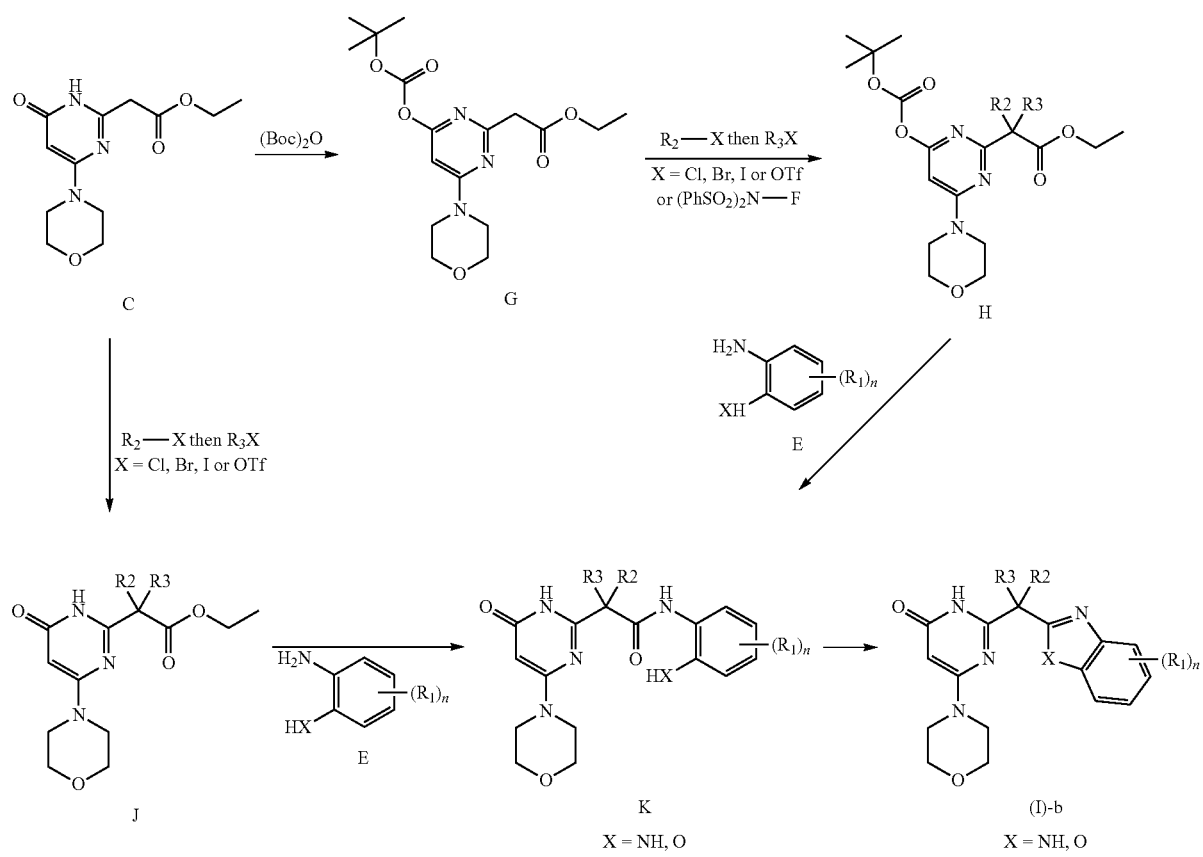

or different, chosen from halogen atoms and alkyl, hydroxyl, oxo, alkoxy, $NH_2$, NHalk and $N(alk)_2$ radicals.

6. A pharmaceutical composition comprising at least one compound of claim 1, or a pharmaceutically acceptable addition salt with an inorganic acid or organic acid or with an inorganic or organic base thereof, and a pharmaceutically acceptable carrier.

7. A method of treating cancer, capable of being modulated by inhibition of AKT phosphorylation, in a patient, said method comprising administering to a patient in need thereof a compound of claim 1.

8. The method of claim 7, wherein the cancer is a solid or liquid tumour.

9. The method of claim 7, wherein the cancer is resistant to cytotoxic agents.

10. The method of claim 7, wherein the cancer is a primary tumour.

11. The method of claim 7, wherein the cancer is metastatic.

12. The method of claim 7, wherein the cancer is selected from the group consisting of gastric cancer, hepatic cancer, renal cancer, ovarian cancer, colon cancer, prostate cancer, endometrial cancer, lung (NSCLC and SCLC) cancer, glioblastomas, thyroid cancer, bladder cancer, breast cancers, melanoma, lymphoid or myeloid hematopoietic tumours, sarcomas, brain cancer, larynx cancer, lymphatic system cancer, bone cancer, pancreatic cancer and hamartomas.

13. The compound of formula (I) as defined in claim 1, for the use thereof in chemotherapy of cancer capable of being modulated by inhibition of AKT phosphorylation, alone or in combination.

14. The compound of formula (I) as defined in claim 1 as inhibitors of AKT(PKB) phosphorylation.

* * * * *

UNITED STATES PATENT AND TRADEMARK OFFICE
CERTIFICATE OF CORRECTION

| | | |
|---|---|---|
| PATENT NO. | : 8,507,483 B2 | Page 1 of 1 |
| APPLICATION NO. | : 13/331199 | |
| DATED | : August 13, 2013 | |
| INVENTOR(S) | : Victor Certal et al. | |

It is certified that error appears in the above-identified patent and that said Letters Patent is hereby corrected as shown below:

On the Title Page, Item (54), and in the Specification, Column 1, lines 1-5, in the Title, delete "1 H-Pyrimidin-2-One Derivatives, Preparation Thereof And Pharmaceutical Use Thereof As Inhibitors Of AKT (PKB) Phosphorylation" and insert --6-Morpholin-4-Y1-Pyrimidin-4-(3h)-One Derivatives, And The Pharmaceutical Preparation Thereof As Akt (Pkb) Phosphorylation Inhibitors--.

Signed and Sealed this
Fifteenth Day of July, 2014

Michelle K. Lee
*Deputy Director of the United States Patent and Trademark Office*